US010265419B2

(12) United States Patent
Golijanin

(10) Patent No.: US 10,265,419 B2
(45) Date of Patent: Apr. 23, 2019

(54) INTRAOPERATIVE DETERMINATION OF NERVE LOCATION

(75) Inventor: Dragan Golijanin, Rochester, NY (US)

(73) Assignee: Novadaq Technologies ULC, Burnaby (CA)

( * ) Notice: Subject to any disclaimer, the term of this patent is extended or adjusted under 35 U.S.C. 154(b) by 2466 days.

(21) Appl. No.: 11/515,419

(22) Filed: Sep. 1, 2006

(65) Prior Publication Data

US 2007/0122345 A1 May 31, 2007

Related U.S. Application Data

(60) Provisional application No. 60/713,643, filed on Sep. 2, 2005.

(51) Int. Cl.
*A61N 5/00* (2006.01)
*A61K 49/00* (2006.01)
(52) U.S. Cl.
CPC .................. *A61K 49/0034* (2013.01)
(58) Field of Classification Search
CPC .................. A61B 5/0059; A61B 5/0084
USPC ..... 600/312, 310, 407, 431; 424/9.6; 604/20
See application file for complete search history.

(56) References Cited

U.S. PATENT DOCUMENTS

| 4,109,647 A | 8/1978 | Stern et al. |
|---|---|---|
| 4,162,405 A | 7/1979 | Chance et al. |
| 4,200,801 A | 4/1980 | Schuresko |
| 4,263,916 A | 4/1981 | Brooks et al. |
| 4,394,199 A | 7/1983 | Barnhard, IV et al. |
| 4,473,841 A | 9/1984 | Murakoshi et al. |
| 4,532,918 A | 8/1985 | Wheeler |
| 4,541,438 A | 9/1985 | Parker et al. |
| 4,556,057 A | 12/1985 | Hiruma et al. |
| 4,619,249 A | 10/1986 | Landry |
| 4,718,417 A | 1/1988 | Kittrell et al. |
| 4,719,508 A | 1/1988 | Sasaki et al. |
| 4,768,513 A | 9/1988 | Suzuki |
| 4,773,097 A | 9/1988 | Suzaki et al. |
| 4,774,568 A | 9/1988 | Matsuo |
| 4,786,813 A | 11/1988 | Svanberg et al. |
| 4,805,597 A | 2/1989 | Iwakoshi |
| 4,815,848 A | 3/1989 | Hadeishi |
| 4,821,117 A | 4/1989 | Sekiguchi |
| 4,827,908 A | 5/1989 | Matsuo |
| 4,852,579 A | 8/1989 | Gilstad et al. |
| 4,858,001 A | 8/1989 | Milbank et al. |

(Continued)

FOREIGN PATENT DOCUMENTS

| AT | 409451 B | 8/2002 |
|---|---|---|
| CA | 2212257 A1 | 8/1996 |

(Continued)

OTHER PUBLICATIONS

Dail, W.G., et al., "Multiple vasodilator pathways from the pelvic plexus to the penis of the rat," 1999, *International Journal of Impotence Research*, vol. 11, pp. 277-285.

(Continued)

*Primary Examiner* — Hien Nguyen
(74) *Attorney, Agent, or Firm* — Morrison & Foerster LLP

(57) ABSTRACT

The invention provides methods for intraoperatively determining the location of nerves by use of fluorescent dyes. The methods are particularly useful for locating the cavernous nerves innervating the penis.

13 Claims, 5 Drawing Sheets

(56) References Cited

U.S. PATENT DOCUMENTS

| | | |
|---|---|---|
| 4,860,731 A | 8/1989 | Matsuura |
| 4,867,137 A | 9/1989 | Takahashi |
| 4,868,647 A | 9/1989 | Uehara et al. |
| 4,900,934 A | 2/1990 | Peeters et al. |
| 4,930,516 A | 6/1990 | Alfano et al. |
| 4,938,205 A | 6/1990 | Nudelman |
| 4,957,114 A | 9/1990 | Zeng et al. |
| 4,993,404 A | 2/1991 | Lane |
| 4,995,396 A | 2/1991 | Inaba et al. |
| 4,995,398 A | 2/1991 | Turnidge |
| 4,998,972 A | 3/1991 | Chin et al. |
| 5,003,977 A | 4/1991 | Suzuki et al. |
| 5,042,494 A | 8/1991 | Alfano |
| 5,071,417 A | 12/1991 | Sinofsky |
| 5,078,150 A | 1/1992 | Hara et al. |
| 5,090,400 A | 2/1992 | Saito |
| 5,091,652 A | 2/1992 | Mathies et al. |
| 5,115,137 A | 5/1992 | Andersson-Engels et al. |
| 5,117,466 A | 5/1992 | Buican et al. |
| 5,125,404 A | 6/1992 | Kittrell et al. |
| 5,131,398 A | 7/1992 | Alfano et al. |
| 5,134,662 A | 7/1992 | Bacus et al. |
| 5,165,079 A | 11/1992 | Schulz-Hennig |
| 5,178,616 A | 1/1993 | Uemiya et al. |
| 5,196,928 A | 3/1993 | Karasawa et al. |
| 5,214,503 A | 5/1993 | Chiu et al. |
| 5,225,883 A | 7/1993 | Carter et al. |
| 5,255,087 A | 10/1993 | Nakamura et al. |
| 5,279,298 A | 1/1994 | Flower |
| 5,318,023 A | 6/1994 | Vari et al. |
| 5,318,024 A | 6/1994 | Kittrell et al. |
| 5,318,869 A | 6/1994 | Hashimoto et al. |
| 5,340,592 A | 8/1994 | Goodrich, Jr. et al. |
| 5,361,769 A | 11/1994 | Nilsson |
| 5,365,057 A | 11/1994 | Morley et al. |
| 5,371,355 A | 12/1994 | Wodecki |
| 5,375,603 A | 12/1994 | Feiler |
| 5,377,676 A | 1/1995 | Vari et al. |
| 5,377,686 A | 1/1995 | O'Rourke et al. |
| 5,394,199 A | 2/1995 | Flower |
| 5,419,323 A | 5/1995 | Kittrell et al. |
| 5,420,628 A | 5/1995 | Poulsen et al. |
| 5,421,337 A | 6/1995 | Richards-Kortum et al. |
| 5,421,339 A | 6/1995 | Ramanujam et al. |
| 5,424,841 A | 6/1995 | Van Gelder et al. |
| 5,430,476 A | 7/1995 | Häfele et al. |
| 5,437,274 A | 8/1995 | Khoobehi et al. |
| 5,438,989 A | 8/1995 | Hochman et al. |
| 5,453,448 A | 9/1995 | Narciso, Jr. |
| 5,465,718 A | 11/1995 | Hochman et al. |
| 5,491,343 A | 2/1996 | Brooker |
| 5,496,369 A | 3/1996 | Howard |
| 5,507,287 A | 4/1996 | Palcic et al. |
| 5,514,127 A | 5/1996 | Shanks |
| 5,519,534 A * | 5/1996 | Smith et al. ............... 359/599 |
| 5,576,013 A | 11/1996 | Williams et al. |
| 5,590,660 A | 1/1997 | MacAulay et al. |
| 5,623,930 A | 4/1997 | Wright et al. |
| 5,627,907 A | 5/1997 | Gur et al. |
| 5,647,368 A | 7/1997 | Zeng et al. |
| 5,656,498 A | 8/1997 | Lijima et al. |
| 5,662,644 A | 9/1997 | Swor |
| 5,664,574 A | 9/1997 | Chance |
| 5,673,701 A | 10/1997 | Chance |
| 5,689,241 A | 11/1997 | Clarke, Sr. et al. |
| 5,699,798 A | 12/1997 | Hochman et al. |
| 5,707,986 A | 1/1998 | Miller et al. |
| 5,732,707 A | 3/1998 | Widder et al. |
| 5,741,648 A | 4/1998 | Hemstreet, III et al. |
| 5,743,266 A | 4/1998 | Levene et al. |
| 5,756,541 A | 5/1998 | Strong et al. |
| 5,785,965 A | 7/1998 | Pratt et al. |
| 5,803,914 A | 9/1998 | Ryals et al. |
| 5,827,190 A | 10/1998 | Palcic et al. |
| 5,845,639 A | 12/1998 | Hochman et al. |
| 5,851,181 A | 12/1998 | Talmor |
| 5,865,754 A | 2/1999 | Sevick-Muraca et al. |
| 5,910,510 A | 6/1999 | Strong et al. |
| 5,919,616 A | 7/1999 | Aurelian et al. |
| 5,927,284 A | 7/1999 | Borst et al. |
| 5,935,942 A | 8/1999 | Zeimer |
| 5,951,980 A | 9/1999 | Collen |
| 5,956,435 A | 9/1999 | Buzug et al. |
| 5,965,356 A | 10/1999 | Aurelian et al. |
| 5,999,841 A | 12/1999 | Aoyagi et al. |
| 6,008,889 A | 12/1999 | Zeng et al. |
| 6,013,265 A | 1/2000 | Aurelian |
| 6,021,344 A | 2/2000 | Lui et al. |
| 6,032,070 A | 2/2000 | Flock et al. |
| 6,054,131 A | 4/2000 | Aurelian |
| 6,069,689 A | 5/2000 | Zeng et al. |
| 6,074,627 A | 6/2000 | Dean et al. |
| 6,081,612 A | 6/2000 | Gutkowicz-Krusin et al. |
| 6,093,149 A | 7/2000 | Guracar et al. |
| 6,122,042 A | 9/2000 | Wunderman et al. |
| 6,140,314 A | 10/2000 | Zeimer |
| 6,148,227 A | 11/2000 | Wagnières et al. |
| 6,149,671 A | 11/2000 | Nordquist et al. |
| 6,162,242 A | 12/2000 | Peyman |
| 6,178,340 B1 | 1/2001 | Svetliza |
| 6,179,421 B1 | 1/2001 | Pang |
| 6,186,628 B1 | 2/2001 | Van De Velde |
| 6,196,226 B1 | 3/2001 | Hochman et al. |
| 6,207,168 B1 | 3/2001 | Aurelian |
| 6,211,953 B1 | 4/2001 | Niino et al. |
| 6,217,848 B1 | 4/2001 | Achilefu et al. |
| 6,223,069 B1 | 4/2001 | Pfeiffer et al. |
| 6,233,480 B1 | 5/2001 | Hochman et al. |
| 6,241,672 B1 | 6/2001 | Hochman et al. |
| 6,246,901 B1 | 6/2001 | Benaron |
| 6,248,727 B1 | 6/2001 | Zeimer |
| 6,263,227 B1 | 7/2001 | Boggett et al. |
| 6,272,374 B1 | 8/2001 | Flock et al. |
| 6,280,386 B1 | 8/2001 | Alfano et al. |
| 6,293,911 B1 | 9/2001 | Imasizumi et al. |
| 6,319,273 B1 | 11/2001 | Cheen et al. |
| 6,331,703 B1 * | 12/2001 | Yarnall et al. ............. 250/336.1 |
| 6,335,429 B1 | 1/2002 | Cai et al. |
| 6,351,663 B1 | 2/2002 | Flower et al. |
| 6,351,667 B1 | 2/2002 | Godie |
| 6,353,750 B1 | 3/2002 | Kimura et al. |
| 6,399,354 B1 | 6/2002 | Knipe et al. |
| 6,440,950 B1 | 8/2002 | Zeimer |
| 6,443,976 B1 | 9/2002 | Flower et al. |
| 6,447,443 B1 | 9/2002 | Keogh et al. |
| 6,485,413 B1 | 11/2002 | Boppart et al. |
| 6,498,945 B1 | 12/2002 | Alfheim et al. |
| 6,544,183 B2 | 4/2003 | Thorn Leeson et al. |
| 6,566,641 B1 | 5/2003 | Suda |
| 6,603,552 B1 | 8/2003 | Cline et al. |
| 6,621,917 B1 | 9/2003 | Vilser |
| 6,631,286 B2 | 10/2003 | Pfeiffer et al. |
| 6,671,540 B1 | 12/2003 | Hochman |
| 6,757,554 B2 | 6/2004 | Rubinstein et al. |
| 6,804,549 B2 | 10/2004 | Hayashi |
| 6,821,946 B2 | 11/2004 | Goldspink et al. |
| 6,840,933 B1 | 1/2005 | Pang et al. |
| 6,853,857 B2 | 2/2005 | Pfeiffer et al. |
| 6,882,366 B1 | 4/2005 | Kijima et al. |
| 6,899,675 B2 | 5/2005 | Cline et al. |
| 6,915,154 B1 | 7/2005 | Docherty et al. |
| 6,936,043 B2 | 8/2005 | Peyman |
| 6,944,493 B2 | 9/2005 | Alam et al. |
| 7,113,817 B1 | 9/2006 | Winchester, Jr. et al. |
| 7,236,815 B2 | 6/2007 | Richards-Kortum et al. |
| 7,364,574 B2 | 4/2008 | Flower |
| 7,381,400 B2 | 6/2008 | Woltering |
| 7,400,753 B2 | 7/2008 | Seino et al. |
| 7,400,755 B2 | 7/2008 | West et al. |
| 7,482,318 B2 | 1/2009 | Aurelian et al. |
| 7,581,191 B2 | 8/2009 | Rice et al. |
| 7,729,750 B2 | 6/2010 | Tromberg et al. |
| 7,774,048 B2 | 8/2010 | Nakaoka et al. |
| 7,881,777 B2 | 2/2011 | Docherty et al. |

(56) References Cited

U.S. PATENT DOCUMENTS

| | | |
|---|---|---|
| 7,885,438 B2 | 2/2011 | Uppaluri et al. |
| 8,036,437 B2 | 10/2011 | Arditi et al. |
| 8,073,224 B2 | 12/2011 | Strobel et al. |
| 8,144,958 B2 | 3/2012 | Nahm et al. |
| 8,185,176 B2 | 5/2012 | Mangat et al. |
| 8,194,981 B2 | 6/2012 | Suzuki |
| 8,285,353 B2 | 10/2012 | Choi et al. |
| 8,361,775 B2 | 1/2013 | Flower |
| 8,406,860 B2 | 3/2013 | Dvorsky et al. |
| 8,480,579 B2 | 7/2013 | Serov et al. |
| 8,521,260 B2 | 8/2013 | Grinvald et al. |
| 8,538,107 B2 | 9/2013 | Röttger |
| 8,647,605 B2 | 2/2014 | Mangat et al. |
| 8,725,225 B2 | 5/2014 | Golijanin et al. |
| 8,892,190 B2 | 11/2014 | Docherty et al. |
| 8,929,974 B2 | 1/2015 | Hauger et al. |
| 8,965,488 B2 | 2/2015 | Dvorsky et al. |
| 9,089,601 B2 | 7/2015 | Golijanin et al. |
| 9,129,366 B2 | 9/2015 | Nahm et al. |
| 9,241,636 B2 | 1/2016 | Koizumi et al. |
| RE45,916 E | 3/2016 | Golijanin et al. |
| 9,351,644 B2 | 5/2016 | Nahm et al. |
| 9,357,931 B2 | 6/2016 | Nahm et al. |
| 9,421,280 B2 | 8/2016 | Mangat et al. |
| 9,610,021 B2 | 4/2017 | Dvorsky et al. |
| 9,642,532 B2 | 5/2017 | Fengler et al. |
| 9,816,930 B2 | 11/2017 | Moriyama et al. |
| 9,936,887 B2 | 4/2018 | Dvorsky et al. |
| 10,041,042 B2 | 8/2018 | Flower |
| 2002/0025541 A1 | 2/2002 | Nelson et al. |
| 2002/0038120 A1 | 3/2002 | Duhaylongsod et al. |
| 2002/0099279 A1 | 7/2002 | Pfeiffer et al. |
| 2002/0099295 A1 | 7/2002 | Gil et al. |
| 2002/0146369 A1* | 10/2002 | Goldenberg ............... 424/1.49 |
| 2002/0181752 A1 | 12/2002 | Wallo et al. |
| 2002/0183621 A1 | 12/2002 | Pfeiffer et al. |
| 2003/0032885 A1 | 2/2003 | Rubinstein et al. |
| 2003/0050543 A1 | 3/2003 | Hartmann |
| 2003/0060718 A1 | 3/2003 | Alam et al. |
| 2003/0060722 A1 | 3/2003 | Pfeiffer et al. |
| 2003/0064025 A1 | 4/2003 | Yang et al. |
| 2003/0093064 A1 | 5/2003 | Peyman |
| 2003/0093065 A1 | 5/2003 | Peyman |
| 2003/0156252 A1 | 8/2003 | Morris et al. |
| 2003/0187349 A1 | 10/2003 | Kaneko et al. |
| 2003/0232016 A1 | 12/2003 | Heinrich |
| 2003/0236458 A1* | 12/2003 | Hochman ................ 600/431 |
| 2004/0066961 A1 | 4/2004 | Spreeuwers et al. |
| 2004/0077952 A1 | 4/2004 | Rafter et al. |
| 2004/0109231 A1 | 6/2004 | Haisch et al. |
| 2004/0156782 A1 | 8/2004 | Alam et al. |
| 2004/0162489 A1 | 8/2004 | Richards-Kortum et al. |
| 2004/0171827 A1 | 9/2004 | Peng et al. |
| 2004/0174495 A1* | 9/2004 | Levine ................... 351/205 |
| 2004/0206364 A1 | 10/2004 | Flower |
| 2005/0019744 A1 | 1/2005 | Bertuglia |
| 2005/0020891 A1 | 1/2005 | Rubinstein et al. |
| 2005/0033145 A1 | 2/2005 | Graham et al. |
| 2005/0069525 A1 | 3/2005 | Mikael |
| 2005/0089866 A1* | 4/2005 | Hinuma et al. ................. 435/6 |
| 2005/0107380 A1 | 5/2005 | Nimmo et al. |
| 2005/0142556 A1 | 6/2005 | Hoon et al. |
| 2005/0182321 A1 | 8/2005 | Frangioni |
| 2005/0182327 A1 | 8/2005 | Petty et al. |
| 2005/0182431 A1 | 8/2005 | Hausen et al. |
| 2005/0182434 A1 | 8/2005 | Docherty et al. |
| 2005/0187477 A1 | 8/2005 | Serov et al. |
| 2005/0197583 A1 | 9/2005 | Chance |
| 2005/0254008 A1 | 11/2005 | Ferguson et al. |
| 2006/0013768 A1 | 1/2006 | Woltering |
| 2006/0079750 A1 | 4/2006 | Fauci et al. |
| 2006/0108509 A1 | 5/2006 | Frangioni et al. |
| 2006/0118742 A1 | 6/2006 | Levenson et al. |
| 2006/0147897 A1 | 7/2006 | Grinvald et al. |
| 2006/0239921 A1 | 10/2006 | Mangat et al. |
| 2006/0241499 A1 | 10/2006 | Irion et al. |
| 2007/0122344 A1 | 5/2007 | Golijanin |
| 2007/0203413 A1 | 8/2007 | Frangioni |
| 2007/0254276 A1 | 11/2007 | Deutsch et al. |
| 2008/0007733 A1 | 1/2008 | Marks et al. |
| 2008/0015446 A1 | 1/2008 | Mahmood et al. |
| 2008/0025918 A1 | 1/2008 | Frangioni et al. |
| 2008/0044073 A1 | 2/2008 | Bernhardt et al. |
| 2008/0161744 A1 | 7/2008 | Golijanin et al. |
| 2008/0221421 A1 | 9/2008 | Choi et al. |
| 2008/0221648 A1 | 9/2008 | Flower |
| 2008/0239070 A1 | 10/2008 | Westwick et al. |
| 2008/0319309 A1 | 12/2008 | Bredno et al. |
| 2009/0005693 A1 | 1/2009 | Brauner et al. |
| 2009/0042179 A1 | 2/2009 | Peltie et al. |
| 2009/0048516 A1 | 2/2009 | Yoshikawa et al. |
| 2009/0054788 A1 | 2/2009 | Hauger et al. |
| 2009/0118623 A1 | 5/2009 | Serov et al. |
| 2009/0137902 A1 | 5/2009 | Frangioni et al. |
| 2009/0252682 A1 | 10/2009 | Hillman |
| 2009/0297004 A1 | 12/2009 | Baumgart |
| 2010/0022898 A1 | 1/2010 | Rubinstein et al. |
| 2010/0036217 A1 | 2/2010 | Choi et al. |
| 2010/0061604 A1 | 3/2010 | Nahm et al. |
| 2010/0222673 A1 | 9/2010 | Mangat et al. |
| 2010/0286529 A1 | 11/2010 | Carroll et al. |
| 2011/0001061 A1 | 1/2011 | Ishihara |
| 2011/0013002 A1 | 1/2011 | Thompson et al. |
| 2011/0063427 A1 | 3/2011 | Fengler et al. |
| 2011/0071403 A1 | 3/2011 | Sevick-Muraca et al. |
| 2011/0098685 A1 | 4/2011 | Flower |
| 2011/0306877 A1 | 12/2011 | Dvorsky et al. |
| 2012/0026325 A1 | 2/2012 | Bunker et al. |
| 2012/0078093 A1 | 3/2012 | Flower |
| 2012/0165662 A1 | 6/2012 | Nahm et al. |
| 2012/0271176 A1 | 10/2012 | Moghaddam et al. |
| 2013/0230866 A1 | 9/2013 | Miyashita et al. |
| 2013/0245456 A1 | 9/2013 | Ferguson, Jr. et al. |
| 2013/0286176 A1 | 10/2013 | Westwick et al. |
| 2013/0296715 A1 | 11/2013 | Lasser et al. |
| 2013/0345560 A1 | 12/2013 | Ferguson, Jr. et al. |
| 2014/0099007 A1 | 4/2014 | Sarkar et al. |
| 2014/0308656 A1 | 10/2014 | Flower |
| 2014/0316262 A1 | 10/2014 | Havens |
| 2015/0112192 A1 | 4/2015 | Docherty et al. |
| 2015/0112193 A1 | 4/2015 | Docherty et al. |
| 2015/0196208 A1 | 7/2015 | Dvorsky et al. |
| 2015/0230710 A1 | 8/2015 | Nahm et al. |
| 2015/0230715 A1 | 8/2015 | Nahm et al. |
| 2016/0038027 A1 | 2/2016 | Brzozowski et al. |
| 2016/0041098 A1 | 2/2016 | Hirawake et al. |
| 2016/0199515 A1 | 7/2016 | Flower |
| 2016/0371834 A1 | 12/2016 | Watanabe et al. |
| 2017/0039710 A1 | 2/2017 | Minai et al. |
| 2017/0303800 A1 | 10/2017 | Flower et al. |
| 2018/0020933 A1 | 1/2018 | Dvorsky et al. |
| 2018/0104362 A1 | 4/2018 | Golijanin et al. |
| 2018/0120230 A1 | 5/2018 | Moriyama et al. |
| 2018/0220907 A1 | 8/2018 | Dvorsky et al. |
| 2018/0234603 A1 | 8/2018 | Moore et al. |

FOREIGN PATENT DOCUMENTS

| | | |
|---|---|---|
| CA | 2413033 A1 | 3/2000 |
| CA | 2711560 A1 | 7/2009 |
| CN | 1049781 A | 3/1991 |
| CN | 1200174 A | 11/1998 |
| CN | 1399528 A | 2/2003 |
| CN | 101264014 A | 9/2008 |
| DE | 3906860 A1 | 9/1989 |
| DE | 19608027 A1 | 9/1996 |
| DE | 10028233 A1 | 1/2002 |
| DE | 10120980 A1 | 11/2002 |
| DE | 69727220 T2 | 12/2004 |
| DE | 102005044531 A1 | 3/2007 |
| EP | 0091805 A2 | 10/1983 |
| EP | 0215772 A2 | 3/1987 |
| EP | 0512965 A1 | 11/1992 |
| EP | 0792618 A1 | 9/1997 |

(56) References Cited

FOREIGN PATENT DOCUMENTS

| | | |
|---|---|---|
| EP | 0807402 A1 | 11/1997 |
| EP | 0826335 A1 | 3/1998 |
| EP | 1761171 | 3/2007 |
| EP | 1874181 | 1/2008 |
| GB | 2203831 A | 10/1988 |
| JP | S58-222331 A | 12/1983 |
| JP | S59-069721 A | 4/1984 |
| JP | S59-070903 A | 4/1984 |
| JP | H01-236879 A | 9/1989 |
| JP | 02-200237 A | 8/1990 |
| JP | H03-115958 A | 5/1991 |
| JP | 04-297236 A | 10/1992 |
| JP | H05-264232 A | 10/1993 |
| JP | H06-007353 A | 1/1994 |
| JP | 06-335451 A | 12/1994 |
| JP | H07-043303 A | 2/1995 |
| JP | 07-065154 A | 3/1995 |
| JP | 07-079955 A | 3/1995 |
| JP | H07-155285 A | 6/1995 |
| JP | H07-155286 A | 6/1995 |
| JP | H07-155290 A | 6/1995 |
| JP | H07-155291 A | 6/1995 |
| JP | H07-155292 A | 6/1995 |
| JP | 07-222712 A | 8/1995 |
| JP | H07-204156 A | 8/1995 |
| JP | H07-222723 A | 8/1995 |
| JP | H07-250804 A | 10/1995 |
| JP | H07-250812 A | 10/1995 |
| JP | 08-024227 A | 1/1996 |
| JP | H08-224208 A | 9/1996 |
| JP | H08-224209 A | 9/1996 |
| JP | H08-224240 A | 9/1996 |
| JP | H09-120033 A | 5/1997 |
| JP | H09-305845 A | 11/1997 |
| JP | B-3896176 | 12/1997 |
| JP | H09-308609 A | 12/1997 |
| JP | H09-309845 A | 12/1997 |
| JP | H10-500479 A | 1/1998 |
| JP | H10-503480 A | 3/1998 |
| JP | H10-085222 A | 4/1998 |
| JP | H10-104070 A | 4/1998 |
| JP | H10-151104 A | 6/1998 |
| JP | H10-506440 A | 6/1998 |
| JP | H10-506550 A | 6/1998 |
| JP | H10-201700 A | 8/1998 |
| JP | H10-201707 A | 8/1998 |
| JP | H11-137517 A | 5/1999 |
| JP | H11-155812 A | 6/1999 |
| JP | H11-509748 A | 8/1999 |
| JP | 2001-198079 A | 7/2001 |
| JP | 2002-219129 A | 8/2002 |
| JP | 2003-510121 A | 3/2003 |
| JP | 2003-144401 A | 5/2003 |
| JP | 2003-329589 A | 11/2003 |
| JP | 2004-528917 A | 9/2004 |
| JP | 2004-325200 A | 11/2004 |
| JP | 2006-503620 A | 2/2006 |
| JP | 2006-192280 A | 7/2006 |
| JP | 2007-021006 A | 2/2007 |
| JP | 2008-525126 A | 7/2008 |
| JP | 2008-535600 A | 9/2008 |
| JP | 2008-231113 A | 10/2008 |
| JP | 2009-095683 A | 5/2009 |
| JP | 2009-291554 A | 12/2009 |
| JP | 2010-505582 A | 2/2010 |
| JP | 2011-509768 A | 3/2011 |
| JP | 2011-519589 A | 7/2011 |
| JP | 2011-528918 A | 12/2011 |
| JP | 5918532 B2 | 5/2016 |
| KR | 90-0005434 B1 | 7/1990 |
| KR | 2002-0064287 A | 8/2002 |
| RU | 2288633 C1 | 12/2006 |
| WO | WO-1986/02730 A1 | 5/1986 |
| WO | WO-1990/10219 A1 | 9/1990 |
| WO | WO-1990/12536 A1 | 11/1990 |
| WO | WO 93/25141 A1 | 12/1993 |
| WO | WO-1994/12092 A1 | 6/1994 |
| WO | WO-1995/00171 A1 | 1/1995 |
| WO | WO-1995/26673 A2 | 10/1995 |
| WO | WO-1996/09435 A1 | 3/1996 |
| WO | WO-1996/09792 A1 | 4/1996 |
| WO | WO-1996/18415 A1 | 6/1996 |
| WO | WO-1996/23524 A1 | 8/1996 |
| WO | WO-1996/39925 A1 | 12/1996 |
| WO | WO-1997/08538 A1 | 3/1997 |
| WO | WO-1998/24360 A1 | 6/1998 |
| WO | WO-1998/30144 A1 | 7/1998 |
| WO | WO-1998/46122 A1 | 10/1998 |
| WO | WO-1999/00053 A1 | 1/1999 |
| WO | WO-1999/47940 A1 | 9/1999 |
| WO | WO-1999/53832 A1 | 10/1999 |
| WO | WO-2000/42910 A1 | 7/2000 |
| WO | WO-2000/47107 A1 | 8/2000 |
| WO | WO-2001/08552 A1 | 2/2001 |
| WO | WO-2001/17561 A1 | 3/2001 |
| WO | WO-2001/22870 A1 | 4/2001 |
| WO | WO-2001/39764 A2 | 6/2001 |
| WO | WO-2001/69244 A2 | 9/2001 |
| WO | WO-2001/80734 A1 | 11/2001 |
| WO | WO-2001/82786 A2 | 11/2001 |
| WO | WO-2002/061390 A2 | 8/2002 |
| WO | WO-2003/006658 A1 | 1/2003 |
| WO | WO-2004/006963 A1 | 1/2004 |
| WO | WO-2004/052195 A1 | 6/2004 |
| WO | WO-2005/026319 A2 | 3/2005 |
| WO | WO 2005/034747 A1 | 4/2005 |
| WO | WO-2005/079238 A2 | 9/2005 |
| WO | WO-2006/111836 A1 | 10/2006 |
| WO | WO-2006/111909 A1 | 10/2006 |
| WO | WO-2006/116634 A2 | 11/2006 |
| WO | WO-2006/119349 A2 | 11/2006 |
| WO | WO-2006/121631 A2 | 11/2006 |
| WO | WO-2006/121631 A3 | 11/2006 |
| WO | WO-2006/123742 A1 | 11/2006 |
| WO | WO-2007/028032 A2 | 3/2007 |
| WO | WO-2008/044822 A1 | 4/2008 |
| WO | WO-2008/070269 A2 | 6/2008 |
| WO | WO-2008/070269 A3 | 6/2008 |
| WO | WO-2008/087869 A1 | 7/2008 |
| WO | WO-2009/046985 A2 | 4/2009 |
| WO | WO-2009/046985 A3 | 4/2009 |
| WO | WO-2009/048660 A2 | 4/2009 |
| WO | WO-2009/092162 A1 | 7/2009 |
| WO | WO-2009/127972 A2 | 10/2009 |
| WO | WO-2012/038824 A1 | 3/2012 |
| WO | WO-2012/096878 A2 | 7/2012 |
| WO | WO-2013/190391 A2 | 12/2013 |
| WO | WO-2015/001427 A2 | 1/2015 |
| WO | WO-2013/002350 A1 | 2/2015 |

OTHER PUBLICATIONS

De Grand, A.M. and J.V. Frangioni, "An operational near-infrared fluorescence imaging system prototype for large animal surgery," 2003, *Technology in Cancer Research & Treatment*, vol. 2(6), pp. 1-10.

Frangioni, John V., "In vivo near-infrared fluorescence imaging," 2003, *Current Opinion in Chemical Biology*, vol. 7, pp. 626-634.

Humblet, V., et al., "High-affinity near-infrared fluorescent small-molecule contrast agents for in vivo imaging of prostate-specific membrane antigen," 2005, *Mol. Imaging*, vol. 4(4), pp. 448-462.

Kim, S., et al., "Near-infrared fluorescence type II quantum dots for sentinel lymph node mapping," 2004, *Nature Biotechnology*, vol. 22(1), pp. 93-97.

Liedberg, F., et al., "[Bladder cancer and the sentinel node concept,]" 2003, *Aktuelle Urol.*, vol. 34(2), pp. 115-118.

Liedberg, F., et al., "Intraoperative sentinel node detection improves nodal staging in invasive bladder cancer," 2006, *J. Urol.*, vol. 175, pp. 84-89.

Leissner, J., et al., "Extended radical lymphadenectomy in patients with urothelial bladder cancer: Results of a prospective multicenter study," 2004, *J. Urol.* vol. 171, pp. 139-144.

(56) References Cited

OTHER PUBLICATIONS

Malmström, P-U, et al., "RE: Extended radical lymphadenectomy in patients with urothelial bladder cancer: Results of a prospective multicenter study," 2004, *J. Urol.* vol. 172, p. 386.

Marangos, N., et al., "In vivo visualization of the cochlear nerve and nuclei with fluorescent axonal tracers," 2001, *Hearing Research*, vol. 162, pp. 48-52.

Nakayama, A., et al., "Functional near-infrared fluorescence imaging for cardiac surgery and targeted gene therapy," 2002, *Mol. Imaging*, vol. 1(4), pp. 365-377.

Nimura, H., et al., "Infrared ray electronic endoscopy combined with indocyanine green injection for detection of sentinel nodes of patients with gastric cancer," 2004, *British Journal of Surgery*, vol. 91, pp. 575-579.

Parungo, C.P., et al., "In vivo optical imaging of pleural space drainage to lymph nodes of prognostic significance," 2004, *Annas of Surgical Oncology*, vol. 11(12), pp. 1085-1092.

Parungo, C.P., et al., "Intraoperative identification of esophageal sentinel lymph nodes with near-infrared fluorescence imaging," 2005, *J. Thorac. Cardiovasc. Surg.*, vol. 129, pp. 844-850.

Schneider, HC Jr., et al., "Fluorescence of testicle. An indication of viability of spermatic cord after torsion," 1975, *Urology*, vol. 5(1), pp. 133-136.

Sherif, A., et al., "Lymphatic mapping and detection of sentinel nodes in patients with bladder cancer," 2001, *J. Urol.*, vol. 166, pp. 812-815.

Soltesz, E.G., et al., "Intraoperative sentinel lymph node mapping of the lung using near-infrared fluorescent quantum dots," 2005, *Ann. Thorac. Surg.*, vol. 79, pp. 269-277.

Sugi, K. et al., "Comparison of three tracers for detecting sentinel lymph nodes in patients with clinical N0 lung cancer," 2003, *Lung Cancer*, vol. 39, pp. 37-40.

Uren, Roger F., "Cancer surgery joins the dots," 2004, *Nature Biotechnology*, vol. 22(1), pp. 38-39.

Author Unkown, "Invitrogen," Material Safety Data Sheet, Jun. 4, 2008, pp. 1-4.

Schmued, et al., "Intracranial Injection of Fluoro-Gold Results in the Degeneration of Local but not Retrogradely Labeled Neurons," Brain Research, 1993, pp. 71-77, vol. 626, Elsevier, Maryland Heights, MO, USA.

Naumann, et al., "Retrograde Tracing of Fluoro-Gold: Different Methods of Tracer Detection at the Ultrastructural Level and Neurodegenerative Changes of Back-Filled Neurons in Long-Term Studies," Journal of Neuroscience Methods, 2000, pp. 11-21, vol. 103, Elsevier, Maryland Heights, MO, USA.

He, "Fluorogold Induces Persistent Neurological Deficits and Circling Behavior in Mice Over-Expressing Human Mutant Tau," Current Neurovascular Research, 2009, pp. 54-61, vol. 6, Bentham Science Publishers Ltd., Oak Park, IL, USA.

Garrett, et. al., "Fluoro-Gold's Toxicity Makes It Inferior to True Blue for Long-Term Studies of Dorsal Root Ganglion Neurons and Motoneurons," Neuroscience Letters, 1991, pp. 137-139, vol. 128, Elsevier, Maryland Heights, MO, USA.

Puigdellivol-Sanchez et al., "On the use of fast blue, fluoro-gold and diamidino yellow for retrograde tracing after peripheral nerve injury: uptake, fading, dye interactions, and toxicity," Journal of Neuroscience Methods, 115:115-127, (2002).

Raabe et al., "Near-Infrared Indocyanine Green Video Angiography: A New Method for Intraoperative Assessment of Vascular Flow," Neurosurgery, 52(1):132-139, (2003).

Ross et al., "Sentinel Node Biopsy in Head and Neck Cancer: Preliminary Results of a Multicenter Trial," Annals of Surgical Oncology, 11(7):690-696, (2004).

Ross et al., "The ability of lymphoscintigraphy to direct sentinel node biopsy in the clinically NO neck for patients with head and neck squamous cell carcinoma," The British Journal of Radiology, 75:950-958, (2002).

Rubben et al., "Infrared Videoangiofluorography of the Skin with Indocyanine Green-Rat Random Cutaneous Flap Model and Results in Man," Microvascular Research, 47:240-251, (1994).

Schmued et al., "In vivo anterograde and retrograde axonal transport of the fluorescent rhodamine-dextran-amine, Fluoro-Ruby, within the CNS," Brain Research, 526: 127-134, (1990).

Shoaib et al., "The Accuracy of Head and Neck Carcinoma Sentinel Lymph Node Biopsy in the Clinically NO Neck," 5th International Conference on Head and Neck Cancer, San Francisco, CA, pp. 2077-2083, (2001).

Stoeckli et al., "Sentinel lymph node evaluation in squamous cell carcinoma of the head and neck," 5th International Conference on Head and Neck Cancer, pp. 221-226, Jul. 29-Aug. 3, 2000.

Tubbs et al., "Anatomic Landmarks for Nerves of the Neck: A Vade mecum for Neurosurgeons," Neurosurgery, 56:0NS256-0NS260, (2005).

Valero-Cabre et al., "Superior Muscle Reinnervation After Autologous Nerve Graft or Poly-L-Lactide-ϵ-Caprolactone (PLC) Tube Implantation in Comparison to Silicone Tube Repair," Journal of Neuroscience Research, 63:214-223, (2001).

Jamis-Dow et al., "Small (≤3-cm) Renal Masses: Detection with CT versus US and Pathologic Correlation," Radiology, 198(3):785-788, (1996).

Kamolz et al., "Indocyanine green video angiographies help to identify burns requiring operation," Burns, 29:785-791, (2003).

Kobbert et al., "Current concepts in neuroanatomical tracing," Progress in Neurobiology, 62:327-351, (2000).

Lanciego et al., "Multiple axonal tracing: simultaneous detection of three tracers in the same section," Histochem Cell Biol, 110:509-515, (1998).

Lanciego et al., "Multiple neuroanatomical tracing in primates," Brain Research Protocols, 2:323-332, (1998).

Liptay, "Sentinel Node Mapping in Lung Cancer," Annals of Surgical Oncology, 11(3):271S-274S, (2004).

Malmstrom et al., "Early Metastatic Progression of Bladder Carcinoma: Molecular Profile of Primary Tumor and Sentinel Lymph Node," The Journal of Urology, 168:2240-2244, (2002).

Minciacchi et al., "A procedure for the simultaneous visualization of two anterograde and different retrograde fluorescent tracers," Journal of Neuroscience Methods, 38:183-191, (1991).

Motomura et al. "Sentinel Node Biopsy Guided by Indocyanin Green Dye in Breast Cancer Patients," Jpn J Clin Oncol., 29(12):604-607, (1999).

Paques et al., "Axon-Tracing Properties of Indocyanine Green," Arch Ophthalmol, 121:367-370, (2003).

Akintunde et al., "Quadruple labeling of brain-stem neurons: a multiple retrograde fluorescent tracer study of axonal collateralization," Journal of Neuroscience Methods, 45:15-22, (1992).

Butter et al., "Melanoma in children and the use of sentinel lymph node biopsy," Journal of Pediatric Surgery, 40:797-800, (2005).

Dan et al., "1% Lymphazurin vs 10% Fluorescein for Sentinel Node Mapping in Colorectal Tumors," Arch Surg., 139:1180-1184, (2004).

Demos, "Near-infrared autofluorescence imaging for detection of cancer," Journal of Biomedical Optics, 9(3):587-592, (2004).

Dietz et al., "Indocyanine Green, Evidence of Neurotoxicity in Spinal Root Axons," Anesthesiology, 98(2):516-520, (2003).

Dunne et al., "Value of sentinel lymphonodectomy in head and neck cancer patients without evidence of lymphogenic metastatic disease," Auris Nasus Larynx, 28:339-344, (2001).

Fritzsch et al., "Sequential double labeling with different fluorescent dyes coupled to dextran amines as a tool to estimate the accuracy of tracer application and of regeneration," Journal of Neuroscience Methods, 39:9-17, (1991).

Gipponi et al., "New Fields of Application of the Sentinel Lymph Node Biopsy in the Pathologic Staging of Solid Neoplasms: Review of Literature and Surgical Perspectives," Journal of Surgical Oncology, 85:171-179, (2004).

Glover et al., "Fluorescent dextran-amines used as axonal tracers in the nervous system of the chicken embryo," Journal of Neuroscience Methods, 18:243-254, (1986).

Haglund et al., "Enhanced Optical Imaging of Rat Gliomas and Tumor Margins," Neurosurgery, 35(5):930-941, (1994).

Haglund et al., "Enhanced Optical Imaging of Human Gliomas and Tumor Margins," Neurosurgery, 38(2):308-317, (1996).

(56) References Cited

OTHER PUBLICATIONS

Angelov et al., "Contralateral trigeminal nerve lesion reduces polyneuronal muscle innervation after facial nerve repair in rats," Eur. J. Neurosci., 11:1369-1378 (1999).

Komurcu et al., "Management strategies for peripheral iatrogenic nerve lesions", Annals of Plastic Surgery, 54 (2):135-139 (2005).

Oddi et al., "Intraoperative Biliary Tree Imaging with Cholyl-Lysyl-Fluorescein: An Experimental Study in the rabbit," Surg. Laproscop. Endosc., 6(3):198-200 (1996).

Ohnishi et al., "Organic Alternatives to Quantum Dots for Intraoperative near-Infrared Fluorescent Lymph Node Mapping," Mol. Imaging, 4(3):172-181 (2005).

Kurihara K. et al., "Nerve Staining with Leucomethylene Blue: An Experimental Study" Plastic and Reconstructive Surgery, 73(6):960-964 (1984).

Nahlieli et al., "Intravital Staining with Methylene Blue as an Aid to Facial Nerve Identification in Parotid Gland Surgery," J. Oral Maxillofac. Surg., 59:355-356 (2001).

U.S. Appl. No. 12/063,349, filed May 10, 2010 in the name of Mangat et al.

U.S. Appl. No. 11/851,312, filed Sep. 6, 2007 in the name of Golijanin et al.

Alander, J.T. et al. (Jan. 1, 2012). "A Review of Indocyanine Green Fluorescent Imaging in Surgery," *International Journal of Biomedical Imaging* 2012:1-26, article ID 940585.

Alfano et al. (Oct. 1987). "Fluorescence Spectra from Cancerous and Normal Human Breast and Lung Tissues," *IEEE Journal of Quantum Electronics* QE-23(10):1806-1811.

Alm, A. et al. (Jan. 1, 1973). "Ocular and Optic Nerve Blood Flow at Normal and Increased Intraocular Pressures in Monkeys (Macaca irus): A Study with Radioactively Labelled Microspheres Including Flow Determinations in Brain and Some Other Tissues," *Experimental Eye Research* 15(1):15-29.

Alonso-Burgos, A. et al. (2006). "Preoperative planning of deep inferior epigastric artery perforator flap reconstruction with multi-slice-CT angiography: imaging findings and initial experience," *Journal of Plastic, Reconstructive & Aesthetic Surgery* 59:585-593.

Alvarez, F. J. et al. (Apr. 1996). "Behaviour of Isolated Rat and Human Red Blood Cells Upon Hypotonic-Dialysis Encapsulation of Carbonic Anhydrase and Dextran," *Biotechnology and Applied Biochemistry* 23(2):173-179.

Ancalmo, N. et al. (1997). "Minimally invasive coronary artery bypass surgery: really minimal?" *Ann. Thorac. Surg.* 64:928-929.

Andersson-Engels, S. et al. (1991). "Fluorescence Characteristics of Atherosclorotic Plaque and Malignant Tumors," in *Optical Methods for Tumor Treatment and Early Diagnosis: Mechanisms and Techniques,* T. J. Dougherty (Ed.), The Society of Photo-optical Instrumentation Engineers (SPIE) 1426:31-43, fourteen pages.

Andersson-Engels, S. et al. (Mar. 1989). "Tissue Diagnostics Using Laser-Induced Fluorescence," *Berichte der Bunsengesellschaft für physikalische Chemie* 93(3):335-342.

Annese, V. et al. (2005). "Erthrocytes-Mediated Delivery of Dexamethasone in Steroid-Dependent IBD Patients—a Pilot Uncontrolled Study," *American Journal of Gastroenterology* 100:1370-1375.

Argus-50/CA, Inter cellular CA2+ (calcium ion) Image Analysis system (Feb. 1992). "Observation and 2-dimensional analysis of Ca2+ concentration distribution. Fura-2 and Indo-1 compatible. Ca2+ concentrations are calculated from the fluorescence ratio," pp. 1-10.

Awano, T. et al. (Jun. 2010). "Intraoperative EC-IC Bypass Blood Flow Assessment with Indocyanine Green Angiography in Moyamoya and Non-moyamoya Ischemic Stroke," *World Neurosurg.* 73(6):668-674.

Azuma, R. et al. (2008, presented in part Jun. 2007). "Detection of Skin Perforators by Indocyanine Green Fluorescence Nearly Infrared Angiography," *PRS Journal* 122(4):1062-1067.

Balacumarswami, L. et al. (Aug. 2004). "Does Off-Pump Total Arterial Grafting Increase the Incidence of Intraoperative Graft Failure?," *The Journal of Thoracic and Cardiovascular Surgery* 128(2):238-244.

Barton, J.K. et al. (1999) "Simultaneous irradiation and imaging of blood vessels during pulsed laser delivery," *Lasers in Surgery and Medicine* 24(3):236-243.

Bassingthwaighte, J.B. et al. (Apr. 1974). "Organ Blood Flow, Wash-in, Washout, and Clearance of Nutrients and Metabolites," *Mayo Clin. Proc.* 49(4):248-255.

Batliwala, H. et al. (Apr. 15, 1995). "Methane-Induced Haemolysis of Human Erythrocytes," *Biochemical J.* 307(2):433-438.

Bek, T. (1999). "Diabetic Maculopathy Caused by Disturbances in Retinal Vasomotion: A New Hypothesis," *Acta Ophthalmologica Scandinavica* 77:376-380.

Benson, R.C. et al. (1978). "Fluorescence Properties of Indocyanine Green as Related to Angiography," *Phys. Med. Biol.* 23(1):159-163.

Black's Medical Dictionary, "Perfusion," 42nd Edition (2009), two pages.

Boer, F.et al. (1994). "Effect of Ventilation on First-Pass Pulmonary Retention of Alfentaril and Sufentanil in Patients Undergoing Coronary Artery Surgery," *British Journal Anesthesia* 73:458-463.

Boldt, .J. et al. (Feb. 1990). "Lung management during cardiopulmonary bypass: influence on extravascular lung water," *Journal of Cardiothoracic Anesthesia* 4(1):73-79.

Boldt, J. et al. (1991). "Does the technique of cardiopulmonary bypass affect lung water content?" *European Journal of Cardio-Thoracic Surgery* 5:22-26.

C2741, Compact High Performance video camera for industrial applications with Built-in contrast enhancement circuit, Jun. 1998, six pgs.

Canada Health. (1997). "Coronary Bypass Surgery and Angioplasty, 1982-1995, Heart Disease and Stroke in Canada," Canada Health, located at <http:/www.hc-sc.gc.ca/hpb>, eighty two pages.

Coffey, J.H. et al. (1984). "Evaluation of Visual Acuity During Laser Photoradiation Therapy of Cancer," *Lasers in Surgery and Medicine* 4(1):65-71.

Conley, M.P. et al. (Oct. 2004). "Anterograde Transport of Peptide-Conjugated Fluorescent Beads in the Squid Giant Axom Identifies a Zip-Code for Synapse," *Biological Bulletin* 207(2):164, one page.

Costa, R.A. et al. (Oct. 2001). "Photodynamic Therapy with Indocyanine Green for Occult Subfoveal Choroidal Neovascularization Caused by Age-Related Macular Degeneration," *Curr. Eye Res.* 23(4):274-275.

Cothren, R.M. et al. (Mar. 1990). "Gastrointestinal Tissue Diagnosis by Laser-Induced Fluorescence Spectroscopy at Endoscopy," *Gastrointestinal Endoscopy* 36(2):105-111.

Daniels, G. et al. (Apr. 2007). "Towards Universal Red Blood Cell," *Nature Biotechnology* 25(4):427-428.

De Flora, A. (Sep. 1986). "Encapsulation of Adriamycin in human erythrocytes," *Proc. Natl. Acad. Sci., USA* 83(18):7029-7033.

Declaration of Brian Wilson dated Aug. 22, 2017 for Inter Partes Review No. IPR2017-01426, twelve pages.

Definition of "Expose," Excerpt of Merriam Webster's Medical Desk Dictionary (1993), four pages.

Definition of "Graft," Excerpt of Stedman's Medical Dictionary for the Health Professions and Nursing; 6th Ed. (2008), three pages.

Deloach, J.R. (ed.) et al. (1985). *Red Blood Cells as Carriers for Drugs. A Method for Disseminating Chemotherapeutics, Hormones, Enzymes and Other Therapeutic Agents via the Circulatory System,* Karger, Basel, CH, pp. v-vii, (Table of Contents), seven pages.

Deloach, J.R. (Jun. 1983). "Encapsulation of Exogenous Agents in Erythrocytes and the Circulating Survival of Carrier Erythrocytes," *Journal of Applied Biochemistry* 5(3):149-157.

Desai, N.D. et al. (Oct. 18, 2005, e-published on Sep. 28, 2005) "Improving the Quality of Coronary Bypass Surgery with Intraoperative Angiography," *Journal of the American College of Cardiology* 46(8):1521-1525.

Detter, C. et al. (Aug. 1, 2007). "Fluorescent Cardiac Imaging: A Novel Intraoperative Method for Quantitative Assessment of Myocardial Perfusion During Graded Coronary Artery Stenosis," *Circulation* 116(9):1007-1014.

(56) References Cited

OTHER PUBLICATIONS

Detter, C. et al. (Jun. 2011). "Near-Infrared Fluorescence Coronary Angiography: A New Noninvasive Technology for Intraoperative Graft Patency Control." *The Heart Surgery Forum #2001-6973* 5(4):364-369.

Digital CCD Microscopy (date unknown). Chapter 14, pp. 259-282.

Dougherty, T.J. et al. (1990). "Cutaneous Phototoxic Occurrences in Patients Receiving Photofrin," *Lasers in Surgery and Medicine* 10(5):485-488.

Draijer, M.J. et al. (Jun. 17-19, 2007). "Laser Doppler Perfusion Imaging with a High-Speed CMOS-Camera," in *Novel Optical Instrumentation for Biomedical Applications III*, C. Depeursinge, ed., Proceedings of SPIE-OSA Biomedical Optics (Optical Society of America, 2007), SPIE-OSA, 6631:0N1-0N7, nine pages.

Ekstrand, M.I. et al. (Feb. 14, 2008). "The Alpha-Herpesviruses: Molecular Pathfinders in Nervous System Circuits," *Trends in Molecular Medicine, Elsevier Current Trends* 14(3):134-140.

Emery R.W. et al. (Aug. 1996). "Revascularization Using Angioplasty and Minimally Invasive Techniques Documented by Thermal Imaging," *The Annals of Thoracic Surgery* 62(2):591-593.

Enquist, L.W. et al. (2002). "Directional Spread of an α-Herpesvirus in the Nervous System," *Veterinary Microbiology* 86:5-16.

Eren, S. et al. (Dec. 1995). "Assessment of Microcirculation of an Axial Skin Flap Using Indocyanine Green Fluorescence Angiography," *Plast. Reconstr. Surg.* 96(7):1636-1649.

Falk, T. et al. (Apr. 15, 2001). "A Herpes Simplex Viral Vector Expressing Green Fluorescent Protein can be Used to Visualize Morphological Changes in High-density Neuronal Culture," *Electronic Journal of Biotechnology* 4(1):34-45.

Flower, R. et al. (Apr.-Jun. 1999). "Effects of free and liposome-encapsulated hemoglobin on choroidal vascular plexus blood flow, using the rabbit eye as a model system," *European Journal of Ophthalmology* 9 (2):103-114.

Flower, R.W. (1992). "Choroidal Angiography Today and Tomorrow," *Retina* 12(3):189-190.

Flower, R.W. (Apr. 2000). "Experimental Studies of Indocyanine Green Dye-Enhanced Photocoagulation of Choroidal Neovascularization Feeder Vessels," *American Journal of Ophthalmology* 129(4):501-512.

Flower, R.W. (Aug. 2002). "Optimizing Treatment of Choroidal Neovascularization Feeder Vessels Associated with Age-Related Macular Degeneration," *American Journal of Ophthalmology* 134(2):228-239.

Flower, R.W. (Dec. 1973). "Injection Technique for Indocyanine Green and Sodium Fluorescein Dye Angiography of the Eye," *Investigative Opthamology* 12(12):881-895.

Flower, R.W. (Sep. 1, 1994). "Does Preinjection Binding of Indocyanine Green to Serum Actually Improve Angiograms?," *Arch Ophthalmol.* 112(9):1137-1139.

Flower, R.W. et al. (Aug. 1977). "Quantification of Indicator Dye Concentration in Ocular Blood Vessels," *Exp. Eye Res.* 25(2):103-111.

Flower, R.W. et al. (Dec. 1, 2008, e-published Aug. 15, 2008). "Observation of Erythrocyte Dynamics in the Retinal Capillaries and Choriocapillaris Using ICG-Loaded Erythrocyte Ghost Cells," *Investigative Ophthalmology, & Visual Science* 49(12):5510-5516.

Flower, R.W. et al. (Mar. 26, 2008-Mar. 29, 2008). "Observation of Erythrocyte Dynamics in the Retinal Capillaries and Choriocapillaris Using ICG-Loaded Erythrocyte Ghost Cells," Annual Meeting of the Macula Society, Abstract No. XP002535355, Palm Beach, FL, USA, fourteen pages, (Schedule of the Meeting only).

Forrester et al. (Nov. 1, 2002). "Comparison of Laser Speckle and Laser Doppler Perfusion Imaging: Measurement in Human Skin and Rabbit Articular Tissue," *Medical and Biological Engineering and Computing* 40(6):687-697.

Frenzel H. et al. (Apr. 18, 2008). "In Vivo Perfusion Analysis of Normal and Dysplastic Ears and its Implication on Total Auricular Reconstruction," *Journal of Plastic, Reconstructive and Aesthetic Surgery* 61(Supplement1):S21-S28.

Gagnon, A.R. et al. (2006). "Deep and Superficial Inferior Epigastric Artery Perforator Flaps," *Cirugia Plástica Ibero-Latinoamericana* 32(4):7-13.

Gardner, T.J. (1993). "Coronary Artery Disease and Ventricular Aneurysms," in *Surgery, Scientific Principles and Practice*, Greenfield, L.J. (ed.) et al., J.B. Lippincott Co., Philadelphia, PA, pp. 1391-1411, twenty three pages.

Geddes, C. D. et al. (2003, e-published on Mar. 20, 2003). "Metal-Enhanced Fluorescence (MEF) Due to Silver Colloids on a Planar Surface: Potential Applications of Indocyanine Green to in Vivo Imaging," *Journal of Physical Chemistry A* 107(18):3443-3449.

Giunta, R.E. et al. (Jul. 2005). "Prediction of Flap Necrosis with Laser Induced Indocyanine Green Fluorescence in a Rat Model," *British Journal of Plastic Surgery* 58(5):695-701.

Giunta, R.E. et al. (Jun. 2000). "The Value of Preoperative Doppler Sonography for Planning Free Perforator Flaps," *Plastic and Reconstructive Surgery* 105(7):2381-2386.

Glossary, Nature, downloaded from the internet <http://www.nature.com/nrg/journal/v4/nI0/glossary/nrgl 183_glossary.html>> HTML on Jun. 30, 2014.

Goldstein, J.A. et al. (Dec. 1998). "Intraoperative Angiography to Assess Graft Patency After Minimally Invasive Coronary Bypass," *Ann. Thorac. Surg.* 66(6):1978-1982.

Gothoskar A.V. (Mar. 2004). "Resealed Erythrocytes: A Review," *Pharmaceutical Technology* pp. 140, 142, 144, 146, 148, 150, 152 and 154-158, twelve pages.

Granzow, J.W. et al. (Jul. 2007)."Breast Reconstruction with Perforator Flaps" *Plastic and Reconstructive Surgery* 120(1):1-12.

Green, H.A. et al. (Jan. 1992). "Burn Depth Estimation Using Indocyanine Green Fluorescence," *Arch Dermatol* 128(1):43-49.

Hallock, G.G. (Jul. 2003). "Doppler sonography and color duplex imaging for planning a perforator flap," *Clinics in Plastic Surgery* 30(3):347-357.

Hamamatsu Brochure. (May 1997). Specifications for Real-time Microscope Image Processing System: ARGUS-20 with C2400-75i, four pages.

Hamamatsu. (Date unknown). Microscope Video Camera, for Fluorescent Observation, Easy Fluorescent Image Analysis C2400-731, -751 Series a CCD Camera, seven pages.

Hayashi, J. et al. (Nov. 1993). "Transadventitial Localization of Atheromatous Plaques by Fluorescence Emission Spectrum Analysis of Mono-L Aspartyl-Chlorin e6," *Cardiovascular Research* 27(11):1943-1947.

Hayata, Y. et al. (Jul. 1982). "Fiberoptic Bronchoscopic Laser Photoradiation for Tumor Localization in Lung Cancer," *Chest*82(1):10-14.

Herts, B.R. (May 2003). "Imaging for Renal Tumors," *Current Opin.. Urol.* 13(3):181-186.

Hirano, T. et al. (1989). "Photodynamic Cancer Diagnosis and Treatment System Consisting of Pulse Lasers and an Endoscopic Spectro-Image Analyzer," *Laser in Life Sciences* 3(2):99-116.

Holm, C. et al. (2002). "Monitoring Free Flaps Using Laser-Induced Fluorescence of Indocyanine Green: A Preliminary Experience," *Microsurgery* 22(7):278-287.

Holm, C. et al. (Apr. 2003, e-published on Feb. 25, 2003). "Laser-Induced Fluorescence of Indocyanine Green: Plastic Surgical Applications," *European Journal of Plastic Surgery* 26(1):19-25.

Holm, C. et al. (Dec. 1, 2002). "Intraoperative Evaluation of Skin-Flap Viability Using Laser-Induced Fluorescence of Indocyanine Green," *British Journal of Plastic Surgery* 55(8):635-644.

Hung, J. et al. (1991). "Autofluorescence of Normal and Malignant Bronchial Tissue," *Lasers in Surgery and Medicine* 11(2):99-105.

Hyvärinen, L. et al. (1980). "Indocyanine Green Fluorescence Angiography." *Acta ophthalmologica* 58(4):528-538.

Ikeda, S. (Jul. 1989). "Bronichial Telivision Endoscopy," *Chest* 96(1):41S-42S.

Jaber, S.F. et al. (Sep. 1998). "Role of Graft Flow Measurement Technique in Anastomotic Quality Assessment in Minimally Invasive CABG," *Ann. Thorac. Surg.* 66(3):1087-1092.

Jagoe, J.R. et al. (1989). "Quantification of retinal damage during cardiopulmonary bypass," Third International Conference on Image Processing and its Applications (Conf. Publ. No. 307), IEE, pp. 319-323.

(56) References Cited

OTHER PUBLICATIONS

Jolion, J. et al. (Aug. 1991). "Robust Clustering with Applications in Computer Vision," *IEEE Transactions on Pattern Analysis and Machine Intelligence* 13(8):791-802.
Kapadia, C.R. et al. (Jul. 1990). "Laser-Induced Fluorescence Spectroscopy of Human Colonic Mucosa. Detection of Adenomatous Transformation," *Gastroenterology* 99(1):150-157.
Kato, H. et al. (Jun. 1985). "Early Detection of Lung Cancer by Means of Hematoporphyrin Derivative Fluorescence and Laser Photoradiation," *Clinics in Chest Medicine* 6(2):237-253.
Kato, H. et al. (Jun. 1990). "Photodynamic Diagnosis in Respiratory Tract Malignancy Using an Excimer Dye Laser System," *Journal of Photochemistry and Photobiology, B. Biology* 6(1-2):189-196.
Keon, W.J. et al. (Dec. 1979). "Coronary Endarterectomy: An Adjunct to Coronary Artery Bypass Grafting," *Surgery* 86(6):859-867.
Kiryu, J. et al. (Sep. 1994). "Noninvasive Visualization of the Choriocapillaris and its Dynamic Filling," *Investigative Ophthalmology & Visual Science* 35(10):3724-3731.
Kitai, T. et al. (Jul. 2005). "Fluorescence Navigation with Indocyanine Green for Detecting Sentinel Lymph Nodes in Breast Cancer," *Breast Cancer* 12(3):211-215.
Kleszcyńska, H. et al. (Mar. 2005). "Hemolysis of Erythrocytes and Erythrocyte Membrane Fluidity Changes by New Lysosomotropic Compounds," *Journal of Fluorescence* 15(2):137-141.
Kokaji, K. et al. (Date Unknown). "Intraoperative Quality Assessment by Using Fluorescent Imaging in Off-pump Coronary Artery Bypass Grafting," *The Department of Cardiovascular Surgery, University of Keio*, Tokyo, Japan, one page, (Abstract only).
Krishnan, K. G. et al. (Apr. 1, 2005). "The Role of Near-Infrared Angiography in the Assessment of Post-Operative Venous Congestion in Random Pattern, Pedicled Island and Free Flaps", *British Journal of Plastic Surgery* 58(3):330-338.
Kuipers, J.A. et al. (1999). "Recirculatory and Compartmental Pharmacokinetic Modeling of Alfentanil Pigs, the Influence of Cardiac Output," *Anesthesiology* 90(4):1146-1157.
Kupriyanov, V.V. et al. (Nov. 2004). "Mapping Regional Oxygenation and Flow in Pig Hearts In Vivo Using Near-infrared Spectroscopic Imaging," *Journal of Molecular and Cellular Cardiology* 37(5):947-957.
Kyo, S. (Date Unknown). "Use of Ultrasound Cardiology during Coronary Artery Bypass Surgery," *Heart and Blood Vessel Imaging II*, three pages.
Lam, S. et al. (1991). "Mechanism of Detection of Early Lung Cancer by Ratio Fluorometry," *Lasers in Life Sciences* 4(2):67-73.
Lam, S. et al. (Feb. 1990). "Detection of Early Lung Cancer Using Low Dose Photofrin II," *Chest* 97(2):333-337.
Lam, S. et al. (Jul. 1, 1990). "Detection of Lung Cancer by Ratio Fluorometry With and Without Photofrin II," *Proc. SPIE—Optical Fibers in Medicine V* 1201:561-568.
Lam, S. et al. (Nov. 1-4, 1990). "Fluorescence Imaging of Early Lung Cancer," *Annual International Conference of the IEEE Engineering in Medicine and Biology Society* 12(3):1142-1143.
Lam, S.C. et al. (1993). "Fluorescence Detection," Chapter 20 in *Lung Cancer*, Roth, J.A. (ed.), et al., Blackwell Scientific Publications Inc., 238 Main Street, Cambridge, Massachusetts, 02142, pp. 325-338, sixteen pages.
Laub, G.W. et al. (Nov. /Dec. 1989). "Experimental Use of Fluorescein for Visualization of Coronary Arteries," *Vascular and Endovascular Surgery* 23(6):454-457.
Lee, E.T. et al. (Mar. 1997). "A New Method for Assessment of Changes in Retinal Blood Flow," *Medical Engineering & Physics* 19(2):125-130.
Leithner, "Untersuchung der Sauerstoffkonzentrationsveranderungen in der Mikrozirkulation des Hirnkortex von Ratten bei funktioneller Stimulation mittels Phosphorescence Quenching," [dissertation], Jul. 14, 2003; retrieved from the Internet: <http://edoc.hu-berlin.de/dissertationen/leith ner-ch ristoph-2003-07-14/>, two hundred and eight pages [English Abstract and Machine Translation].

Lippincott's New Medical Dictionary. "Perfusion," p. 707 (1897), three pages.
Little, J.R. et al. (May 1979). "Superficial Temporal Artery to Middle Cerebral Artery Anastomosis: Intraoperative Evaluation by Fluorescein Angiography and Xenon—133 Clearance," *Journal of Neurosurgery* 50(5):560-569.
Liu Q. P. et al. (Apr. 2007). "Bacterial Glycosidases for the Production of Universal Red Blood Cells" *Nature Biotechnology* 25(7):454-464.
Lund, F. et al. (Nov. 1997). "Video Fluorescein Imaging of the Skin: Description of an Overviewing Technique for Functional Evaluation of Regional Cutaneous Blood Evaluation of Regional Cutaneous Perfusion in Occlusive Arterial Disease of the Limbs," *Clinical Physiology* 17(6):619-633.
Mack, M.J. et al. (Sep. 1998). "Arterial Graft Patency in Coronary Artery Bypass Grafting: What Do We Really Know?," *Ann. Thorac. Surg*. 66(3):1055-1059.
Magnani, M. et al. (1998). "Erythrocyte Engineering for Drug Delivery and Targeting," *Biotechnol. Appl. Biochem*. 28:1-6.
Magnani, M. et al. (Jul. 15, 1992). "Targeting Antiretroviral Nucleoside Analogues in Phosphorylated Form to Macrophasges: In Vitro and In Vivo Studies," *Proc. Natl. Acad. Sci. USA* 89(14):6477-6481.
Martinez-Pérez, M. et al. (Sep. 19, 1996). "Unsupervised Segmentation Based on Robust Estimation and Cooccurrence Data," *Proceedings of the International Conference on Miage Processing (ICIP) Lausanne* 3:943-945.
May, S. (May/Jun. 1995). "Photonic Approaches to Burn Diagnostics," *Biophotonics International* pp. 44-50.
McKee, T.D. et al. (Mar. 1, 2006). "Degradation of Fibrillar Collagen in a Human Melanoma Xenograft Improves the Efficacy of an Oncolytic Herpes Simplex Virus Vector," *Cancer Research* 66(5):2509-2513.
Merriam Webster Medline Plus Medical Dictionary. "Perfusion," located at http://www.merriam-webster.com/medlineplus/perfusion, last visited on Apr. 15, 2015, one page.
Mitaka USA, Inc. (2015). "PDE Breast Free Flap Evaluation," located at <http://mitakausa.com/category/pde_education/flaps/>, last visited on Dec. 29, 2015, four pages.
Mitaka USA, Inc. (2015). "PDE-Neo" located at <http://mitakausa.com/pde-neo/>, last visited on Dec. 29, 2015, two pages.
Mohr, F.W. et al. (May 1997). "Thermal Coronary Angiography: A Method for Assessing Graft Patency and Coronary Anatomy in Coronary Bypass Surgery," *Ann Thorac. Surgery* 63(5):1506-1507.
Montán, S. et al. (Feb. 1, 1985). "Multicolor Imaging and Contrast Enhancement in Cancer-Tumor Localization Using Laser-Induced Fluorescence in Hematoporphyrin-Derivative-Bearing Tissue," *Optics Letters* 10(2):56-58.
Mothes, H. et al. (Nov. 2004). "Indocyanine-Green Fluorescence Video Angiography Used Clinically to Evaluate Tissue Perfusion in Microsurgery," *The Journal of Trauma Injury, Infection, and Critical Care* 57(5):1018-1024.
Mullooly, V.M. et al. (1990). "Dihematoporphyrin Ether-Induced Photosensitivity in Laryngeal Papilloma Patients," *Lasers in Surgery and Medicine* 10(4):349-356.
Murphy (2001). "Digital CCD Microscopy," Chapter 14 in *Fundamentals of Light Microscopy and Electronic Imaging*, John Wiley and Sons, pp. i-xi and 259-281.
Nakamura, T. et al. (1964). "Use of Novel Dyes, Coomassie Blue and Indocyanine Green in Dye Dilution Method," Tohoka University, Nakamura Internal Department, The Tuberculosis Prevention Society, Tuberculosis Research Laboratory, 17(2):1361-1366, seventeen pages.
Newman et al. (Oct. 31, 2008). "Update on the Application of Laser-Assisted Indocyanine Green Fluorescent Dye Angiography in Microsurgical Breast Reconstruction," American Society of Plastic Surgeons, Plastic Surgery 2008, 2 pages.
Novadaq Technologies Inc. (Jan. 29, 2007). "Novadaq Imaging System Receives FDA Clearance for use During Plastic Reconstructive Surgery," *PR Newswire* three pages.
Novadaq Technologies Inc. (Jan. 19, 2005). 510(k) Summary—Showing X-Ray Fluoroscopy as Predicate Device, Fluorescent Angiographic System, six pages.

(56) References Cited

OTHER PUBLICATIONS

Ogata, F. et al. (Jun. 2007). "Novel Lymphography Using Indocyanine Green Dye for Near-Infrared Fluorescence Labeling," *Annals of Plastic Surgery* 58(6):652-655.

Ooyama, M. (Oct. 12-15, 1994). The 8th Congress of International YAG Laser Symposium, The 15th Annual Meeting of Japan Society for Laser Medicine, Sun Royal Hotel, Japan, eight pages.

Ott, P. (1998). "Hepatic Elimination of Indocyanine Green with Special Reference to Distribution Kinetics and the Influence of Plasma Protein Binding," *Pharmacology & Toxicology* 83(Supp. II):5-48.

Oxford Concise Medical Dictionary. "Perfusion," p. 571 (1980), three pages.

Pagni, S. et al. (Jun. 1997). "Anastomotic Complications in Minimally Invasive Coronary Bypass Grafting," *Ann. Thorac. Surg.* 63(6 Suppl):S64-S67.

Palcic et al. (1991). "Lung Imaging Fluorescence Endoscope: A Device for Detection of Occult Lung Cancer," *Medical Design and Material*, thirteen pages.

Palcic, B. et al. (1990). "Development of a Lung Imaging Fluorescence Endoscope," *Annual International Conference of the IEEE Engineering in Medicine and Biology Society* 12(1):0196-0197.

Palcic, B. et al. (Aug. 1, 1990). "The Importance of Image Quality for Computing Texture Features in Biomedical Specimens," *Proc. SPIE* 1205:155-162.

Palcic, B. et al. (Jun. 1, 1991). "Lung Imaging Fluorescence Endoscope: Development and Experimental Prototype," *Proc. SPIE* 1448:113-117.

Palcic, B. et al. (Mar. 1991). "Detection and Localization of Early Lung Cancer by Imaging Techniques," *Chest* 99(3):742-743.

Pandharlpande, P.V. et al. (Mar. 2005). "Perfusion Imaging of the Liver: Current Challenges and Future Goals," *Radiology* 234(3):661-673.

Peak, M.J. et al. (1986). "DNA-to-Protein Crosslinks and Backbone Breaks Caused by FAR-and Near-Ultraviolet and Visible Light Radiations in Mammalian Cells," in *Mechanism of DNA Damage and Repair, Implications for Carcinogenesis and Risk Assessment*, SIMIC, M.G. (ed.) et al., Plenum Press, 233 Spring Street, New York, N.Y. 10013, pp. 193-202.

Peiretti et al. (2005). "Human erythrocyte-ghost-mediated choroidal angiography and photocoagulation." Database Biosis [online] Biosciences Information Service, Philadelphia, PA, US, XP002725023, Database accession No. Prev200600056121 (abstract), three pages.

Peiretti, E. et al. (May 2005). "Human Erythrocyte-Ghost-Mediated Choroidal Angiography and Photocoagulation," *Investigative Ophthalmology & Visual Science*, ARVO Annual Meeting Abstract 46(13):4282, located at <http://iovs.arvojournals.org/article.aspx?articleid=2403707>, last visited on Oct. 7, 2016, two pages.

Perez, M.T. et al. (Sep. 2002). "In Vivo Studies on Mouse Erythrocytes Linked to Transferrin," *IUBMB Life* 54(3):115-121.

Pfister, A.J. et al. (Dec. 1992). "Coronary Artery Bypass Without Cardiopulmonary Bypass," *Ann. Thorac. Surg.* 54(6):1085-1092, (Discussion by S.R. Gundry).

Phillips, R.P. et al. (1991). "Quantification of Diabetic Maculopathy by Digital Imaging of the Fundus," *Eye* 5(1):130-137.

Piermarocchi, S. et al. (Apr. 2002). "Photodynamic Therapy Increases the Eligibility for Feeder Vessel Treatment of Choroidal Neovascularization Caused by Age-Related Macular Degeneration," *American Journal of Ophthalmology* 133(4):572-575.

Profio, A.E. et al. (Jul.-Aug. 1984). "Fluorometer for Endoscopic Diagnosis of Tumors," *Medical Physics* 11(4):516-520.

Profio, A.E. et al. (Jun. 1, 1991). "Endoscopic Fluorescence Detection of Early Lung Cancer," *Proc. SPIE* 1426:44-46.

Profio, A.E. et al. (Nov./Dec. 1979). "Laser Fluorescence Bronchoscope for Localization of Occult Lung Tumors," *Medical Physics* 6:523-525.

Profio, A.E. et al. (Sep.-Oct. 1986). "Digital Background Subtraction for Fluorescence Imaging," *Medical Physics* 13(5):717-721.

Pyner, S. et al. (Nov. 2001). "Tracing Functionally Identified Neurones in a Multisynaptic Pathway in the Hamster and Rat Using Herpes Simplex Virus Expressing Green Fluorescent Protein," *Experimental Physiology* 86(6):695-702.

Raabe et al. (2009, e-published on Nov. 12, 2008). "Laser Doppler Imaging for Intraoperative Human Brain Mapping", *NeuroImage* 44:1284-1289.

Rava, R.P. et al. (Jun. 1, 1991). "Early Detection of Dysplasia in Colon and Bladder Tissue Using Laser-Induced Fluorescence," *Proc. SPIE* 1426:68-78.

Razum, N. et al. (Nov. 1987). "Skin Photosensitivity: Duration and Intensity Following Intravenous Hematoporphyrin Derivatives, HpD and DHE," *Photochemistry and Photobiology* 46(5):925-928.

Report on Observation by C2400-75i and ARGUS20 Under Low illumination conditions, Jan. 17, 2008.

Request for Invalidation mailed on Jun. 29, 2007 for Japanese Patent No. JP-3881550, filed by Hamamatsu Photonics, Inc. (with English Translation).

Reuthebuch, O et al. (Feb. 2004). "Novadaq SPY: Intraoperative Quality Assessment in Off Pump Coronary Artery Bypass Grafting," *Chest* 125(2):418-424.

Reuthebuch, O.T. et al. (May 2003). "Graft Occlusion After Deployment of the Symmetry Bypass System," *Ann. Thorac. Surg.* 75(5):1626-1629.

Richards-Kortum, R. et al. (Jun. 1991). "Spectroscopic Diagnosis of Colonic Dysplasia: Spectroscopic Analysis," *Biochemistry and Photobiology* 53(6):777-786.

Roberts, W.W. et al. (Dec. 1997). "Laparoscopic Infrared Imaging," *Surg. Endoscopy* 11(12):1221-1223.

Rodnenkov, O.V. et al. (May 2005). "Erythrocyte Membrane Fluidity and Haemoglobin Haemoporphyrin Conformation: Features Revealed in Patients with Heart Failure," *Pathophysiology* 11(4):209-213.

Ropars, C. (ed.) et al. (1987). *Red Blood Cells as Carriers for Drugs. Potential therapeutic Applications.* Pergamon Press, Oxford, New York, pp. v-vii, (Table of Contens only), four pages.

Ross, G.L. et al. (Dec. 2002). "The Ability of Lymphoscintigraphy to Direct Sentinel Node Biopsy in the Clinically N0 Neck for Patients with Head and Neck Squamous Cell Carcinoma," *The British Journal of Radiology* 75(900):950-958.

Rossi, L. et al. (2001). "Erthrocyte-Mediated Delivery of Dexamethasone in Patients with Chronic Obstructive Pulmonary Disease," *Biotechnol. Appl. Biochem.* 33:85-89.

Rossi, L. et al. (1999). "Heterodimer-Loaded Erthrocytes as Bioreactors for Slow Delivery of the Antiviral Drug Azidothymidine and the Antimycobacterial Drug Ethambutol," *Aids Research and Human Retroviruses* 15(4):345-353.

Rossi, L. et al. (2004). "Low Doses of Dexamethasone Constantly Delivered by Autologous Erythrocytes Slow the Progression of Lung Disease in Cystic Fibrosis Patients," *Blood Cells, Molecules, and Diseases* 33:57-63.

Rozen, W.M. et al. (Jan. 2008). "Preoperative Imaging for DIEA Perforator Flaps: A Comparative Study of Computed Tomographic Angiography and Doppler Ultrasound," *Plastic and Reconstructive Surgery* 121(1):9-16.

Rubens, F.D. et al. (2002). "A New and Simplified Method for Coronary and Graft Imaging During CABG," *The Heart Surgery Forum* 5(2):141-144.

Sakatani, K. et al. (Nov. 1997). "Noninvasive Optical Imaging of the Subarchnoid Space and Cerebrospinal Fluid Pathways Based on Near Infrared Fluorescence," *J. Neurosurg.* 87(5):738-745.

Salmon, E.D. et al. (Oct. 1994). "High Resolution Multimode Digital Imaging System for Mitosis Studies in Vivo and in Vitro," *Biol. Bull* 187(2):231-232.

Sato, et al., (1991). "Development of a Visualization Method for the Microcirculation of Deep Viscera Using an Infrared Intravital Microscope System," *Research on ME Devices and ME Technology*, five pages, (with English translation).

Satpathy G.R. et al. (Oct. 2004) "Loading Red Blood Cells with Trehalose: A Step Towards Biostabilization," *Cryobiology* 49(2):123-136.

Schaff, H.V. et al. (Oct. 15, 1996). "Minimal Thoracotomy for Coronary Artery Bypass: Value of Immediate Postprocedure Graft Angiography," *Supplement to Circulation* 94(8):I-51, (Abstract No. 0289), two pages.

(56) References Cited

OTHER PUBLICATIONS

Schellingerhout, D. et al. (Oct. 2000). "Quantitation of HSV Mass Distribution in a Rodent Brain Tumor Model," *Gene Therapy* 7(19):1648-1655.
Seeman, P. (Jan. 1, 1967). "Transient Holes in the Erythrocyte Membrane During Hypotonic Hemolysis and Stable Holes in the Membrane After Lysis by Saponin and Lysolecithin," *Journal of Cell Biology* 32(1):55-70.
Sekijima, M. et al. (Sep. 2004). "An Intraoperative Fluorescent Imaging System in Organ Transplantation," *Transplantation Proceedings* 36(7):2188-2190.
Serov, A. et al. (Mar. 1, 2002). "Laser Doppler Perfusion Imaging with a Complimentary Metal Oxide Semiconductor Image Sensor," *Optics Letters* 27(5):300-302.
Serov, A.N. et al. (Sep. 23, 2003). "Quasi-Parallel Laser Doppler Perfusion Imaging Using a CMOS Image Sensor," *Proc. SPIE* 5067:73-84.
Sezgin, M. et al. (Jan. 2004). "Survey Over Image Thresholding Techniques and Quantitative Performance Evaluation," *Journal of Electronic Imaging* 13(1):146-165.
Sheth, S.A. et al. (Apr. 22, 2004)"Linear and Nonlinear Relationships between Neuronal Activity, Oxygen Metabolism, and Hemodynamic Responses," *Neuron* 42(2):347-355.
Siemers, B.M. et al. (Nov. 2001). "The Acoustic Advantage of Hunting at Low Heights Above Water: Behavioual Experiments on the European 'Trawling' Bats Myotis Capaccinii, M Dasycneme and M. Daubentonii," *J. Eperimental Biol*. 204(Pt. 22):3843-3854.
Skalidis, E.I. et al. (Nov. 16, 2004). "Regional Coronary Flow and Contractile Reserve in Patients with Idiopathic Dilated Cardiomyopathy," *Journal of the American College of Cardiology* 44(10):2027-2032.
Slakter, J.S. et al. (Jun. 1995). "Indocyanine-Green Angiography," *Current Opinion in Ophthalmology* 6(III):25-32.
Smith, G.A. et al. (Mar. 13, 2001). "Herpesviruses Use Bidirectional Fast-Axonal Transport to Spread in Sensory Neurons," *Proceedings of the National Academy of Sciences of the United States of America* 98(6):3466-3470.
Sony Corporation. The Sony U-Matic Videocassette Recorder, VO-9800, ten pages.
Staurenghi, G. et al. (Dec. 2001)."Combining Photodynamic Therapy and Feeder Vessel Photocoagulation: A Pilot Study," *Seminars in Ophthalmology* 16(4):233-236.
Stern, M.D. (Mar. 6, 1975). "In Vivo Evaluation of Microcirculation by Coherent Light Scattering," *Nature* 254(5495):56-58.
Still, J. et al. (Mar. 1999). "Evaluation of the Circulation of Reconstructive Flaps Using Laser-Induced Fluorescence of Indocyanine Green," *Ann. Plast. Surg.* 42(3):266-274.
Still, J.M. et al. (Jun. 2001). "Diagnosis of Burn Depth Using Laser-Induced Indocyanine Green Fluorescence: A Preliminary Clinical Trial," *Burns* 27(4):364-371.
Subramanian, V.A. et al. (Oct. 15, 1995). "Minimally Invasive Coronary Bypass Surgery: A Multi-Center Report of Preliminary Clinical Experience," *Supplement to Circulation* 92(8):I-645, (Abstract No. 3093), two pages.
Sugimoto, K. et al. (Jun. 2008, e-published on Mar. 19, 2008). "Simultaneous Tracking of Capsid, Tegument, and Envelope Protein Localization in Living Cells Infected With Triply Fluorescent Herpes Simplex Virus 1," *Journal of Virology* 82(11):5198-5211.
Suma, H. et al. (2000). "Coronary Artery Bypass Grafting Without Cardiopulmonary Bypass in 200 Patients," *J. Cardiol.* 36(2):85-90, (English Abstract only).
Summary of Invention Submitted to EPO, "Development of Novadaq SPY™ Cardiac Imaging Invention," five pages.
Taggart, D.P. et al. (Mar. 2003). "Preliminary Experiences with a Novel Intraoperative Fluorescence Imaging Technique to Evaluate the Patency of Bypass Grafts in Total Arterial Revascularization," *Ann Thorac Surg.* 75(3):870-873.
Taichman, G.C. et al. (Jun. 1987). "The Use of Cardio-Green for Intraoperative Visualization of the Coronary Circulation: Evaluation of Myocardial Toxicity," *Texas Heart Institute Journal* 14(2):133-138.

Takahashi, M. et al. (Sep. 2004). "SPY: An Innovative Intra-Operative Imaging System to Evaluate Graft Patency During Off-Pump Coronary Artery Bypass Grafting," *Interactive Cardio Vascular and Thoracic Surgery* 3(3):479-483.
Takayama, T. et al. (Apr. 1992). "Intraoperative Coronary Angiography Using Fluorescein Basic Studies and Clinical Application," *Vascular and Endovascular Surgery* 26(3):193-199.
Takayama, T. et al. (Jan. 1991). "Intraoperative Coronary Angiography Using Fluorescein" *The Annals of Thoracic Surgery* 51(1):140-143.
Tanaka, E. et al. (Jul. 2009). "Real-time Assessment of Cardiac Perfusion, Coronary Angiography, and Acute Intravascular Thrombi Using Dual-channel Near-infrared Fluorescence Imaging," *The Journal of Thoracic and Cardiovascular Surgery* 138(1):133-140.
Tang, G.C. et al. (1989). "Spectroscopic Differences between Human Cancer and Normal Lung and Breast Tissues," *Lasers in Surgery and Medicine* 9(3):290-295.
Taylor, K.M. (Apr. 1998). "Brain Damage During Cardiopulmonary Bypass," *Annals of Thoracic Surgery* 65(4):S20-S26.
The American Heritage Medical Dictionary. "Perfuse." p. 401 (2008), three pages.
Thelwall, P.E. et al. (Oct. 2002). "Human Erythrocyte Ghosts: Exploring the Origins of Multiexponential Water Diffusion in a Model Biological Tissue with Magnetic Resonance," *Magnetic Resonance in Medicine* 48(4):649-657.
Torok, B. et al. (May 1996). "Simultaneous Digital Indocyanine Green and Fluorescein Angiography," *Klinische Monatsblatter Fur Augenheilkunde* 208(5):333-336, (Abstract only), two pages.
Tsutsumi, D. et al. "Moisture Detection of road surface using infrared camera," Reports of the Hokkaido Industrial Research Institute (No. 297), Issued on Nov. 30, 1998, two pages.
Unno, N. et al. (Feb. 2008, e-published on Oct. 26, 2007). "Indocyanine Green Fluorescence Angiography for intraoperative assessment of Blood flow: A Feasibility Study," *Eur J Vasc Endovasc Surg.* 35(2):205-207.
Van Son, J.A.M. et al. (Nov. 1997). "Thermal Coronary Angiography for Intraoperative Testing of Coronary Patency in Congenital Heart Defects," *Ann Thorac Surg.* 64(5):1499-1500.
Verbeek, X. et al. (2001). "High-Resolution Functional Imaging With Ultrasound Contrast Agents Based on RF Processing in an In Vivo Kidney Experiment", *Ultrasound in Med. & Biol.* 27(2):223-233.
Wachi, A. et al. (Apr. 1995). "Characteristics of Cerebrospinal Fluid Circulation in Infants as Detected With MR Velocity Imaging," *Child's Nerv Syst* 11(4):227-230.
Wagnieres, G.A. et al. (Jul. 1, 1990). "Photodetection of Early Cancer by Laser Induced Fluorescence of a Tumor-Selective Dye: Apparatus Design and Realization," *Proc. SPIE* 1203:43-52.
Weinbeer, M. et al. (Nov. 25, 2013). "Behavioral Flexibility of the Trawling Long-Legged Bat, Macrophyllum Macrophyllum (Phyllostomidae)," *Frontiers in Physiology* 4(Article 342):1-11.
What is Perfusion? A Summary of Different Typed of Perfusion. (Sep. 1, 2004). Located at, <http://www.perfusion.com/cgi-bin/absolutenm/templates/articledisplay.asp?articleid=1548#.Vo8HvO2FPGj>, last visited on Jan. 7, 2016, two pages.
Wise, R.G. et al. (Nov. 2005). "Simultaneous Measurement of Blood and Myocardial Velocity in the Rat Heart by Phase Contrast MRI Using Sparse q-Space Sampling" *Journal of Magnetic Resonance Imaging* 22(5):614-627.
Woitzik, J. et al. (Apr. 2005). "Intraoperative Control of Extracranial-Intracranial Bypass Patency by Near-Infrared Indocyanine Green Videoangiography," *J. Neurosurg.* 102(4):692-698.
Wollert, H.G. et al. (Dec. 1989). "Intraoperative Visualization of Coronary Artery Fistula Using Medical Dye," *The Thoracic and Cardiovascular Surg.* 46(6):382-383.
Wu, C. et al. (Apr. 15, 2005). "cGMP (Guanosine 3',5'-Cyclic Monophosphate) Transport Across Human Erythrocyte Membranes," *Biochemical Pharmacology* 69(8):1257-1262.
Yada, T. et al. (May 1993). "In Vivo Observation of Subendocardial Microvessels of the Beating Porcine Heart Using a Needle-Probe Videomicroscope with a CCD Camera," *Circulation Research* 72(5):939-946.

(56) References Cited

OTHER PUBLICATIONS

Yamaguchi, S. et al. (Apr. 2005). "Evaluation of Skin Perfusion After Nipple-Sparing Mastectomy by Indocyanine Green Dye" *Journal of Saitama Medical University*, Japan, 32(2):45-50, (with English Abstract).
Yoneya, S. et al. (Jun. 1998). "Binding Properties of Indocyanine Green in Human Blood," *IOVS* 39(7):1286-1290.
Yoneya, S. et al. (Sep. 1993). "Improved Visualization of the Choroidal Circulation with Indocyanine Green Angiography," *Arch Opthalmol.* 111(9):1165-1166.
Young. I.T. et al. (1993). "Depth of Focus in Microscopy," SCIA '93, Proc. of the 8th Scandinavian Conference on Image Analysis, Tromso, Norway, pp. 493-498, six pages.
Australian Examination Report No. 1 dated Jun. 26, 2018 for Australian Patent Application No. 2014408488, filed on Mar. 31, 2017, nine pages.
Canadian Notice of Allowance dated Jan. 4, 2018 for Canadian Application No. 2,750,760, filed on Jul. 25, 2008, one page.
Canadian Notice of Allowance dated Sep. 27, 2017 for Canadian Application No. 2,811,847, filed on Mar. 20, 2013, one page.
Canadian Office Action dated Feb. 13, 2018 for CA Application No. 2,963,450 filed on Apr. 3, 2017, three pages.
Canadian Office Action dated Feb. 27, 2017 for Canadian Application No. 2,750,760, filed on Jul. 25, 2011, three pages.
Canadian Office Action dated Feb. 28, 2018 for CA Application No. 2,963,987 filed on Mar. 27, 2017, five pages.
Canadian Office Action dated Jan. 19, 2017 for Canadian Application No. 2,914,778 filed on Dec. 8, 2015, four pages.
Canadian Office Action dated Mar. 16, 2016 for CA Application No. 2,750,760 filed on Jan. 23, 2009, five pages.
Canadian Office Action dated Nov. 28, 2017 for Canadian Application No. 2,914,778 filed on Dec. 8, 2015, six pages.
Canadian Office Action dated Oct. 25, 2016 for Canadian Patent Application No. 2,811,847, filed on Sep. 20, 2011, three pages.
Canadian Office Action dated Sep. 30, 2015 for CA Application No. 2,811,847, filed on Sep. 20, 2011, four pages.
Chinese Fifth Office Action dated Dec. 19, 2017 for Chinese Application No. 201180057244.8 filed on Sep. 20, 2011, eleven pages.
Chinese First Office Action dated Apr. 6, 2017 for Chinese Application No. 201510214021.8, filed on May 14, 2009, fifteen pages.
Chinese Fourth Office Action dated Mar. 13, 2017 for Chinese Application No. 201180057244.8 filed on Sep. 20, 2011, twenty pages.
Chinese Office Action dated Jul. 3, 2012, issued in counterpart Chinese Application No. 200980123414.0, eight pages.
Chinese Office Action dated May 23, 2013, issued in counterpart Chinese Application No. 200980123414.0, nineteen pages.
Chinese Office Action dated Nov. 12, 2015 for Chinese Patent Application No. 201180057244.8, filed on Sep. 20, 2010, five pages.
Chinese Second Office Action dated Feb. 8, 2018 for Chinese Application No. 201510214021.8, filed on May 14, 2009, seventeen pages.
Chinese Third Office Action dated Aug. 8, 2016 for Chinese Application No. 201180057244.8 filed on Sep. 20, 2011, eighteen pages.
European Decision in Opposition Proceeding Revoking (Jun. 10, 2010). European Patent No. 1 143 852, thirty pages.
European Decision of European Patent Office Technical Board of Appeal Revoking Counterpart Patent No. 1143852, dated Oct. 23, 2013.
European Decision to Grant dated Apr. 21, 2017 for EP Application No. 09732993.2, filed on Nov. 8, 2010, two pages.
European Decision to Grant dated Mar. 15, 2018 for EP Application No. 09739980.2 filed on Nov. 30, 2010, two pages.
European Extended Search Report dated Apr. 28, 2014 for EP Application No. 09 732 993.2, filed on Apr. 14, 2008, eight pages.
European Extended Search Report dated Feb. 22, 2012 for EP Application No. 09 704 642.9, filed on Jan. 25, 2008, fifteen pages.
European Extended Search Report dated Jan. 28, 2014 for EP Application No. 11 826 475.3, filed on Sep. 20, 2010, six pages.
European Extended Search Report dated Jun. 6, 2018 for EP Application No. 18166591.0 filed on Apr. 10, 2018, six pages.
European Extended Search Report dated May 23, 2018 for EP Application No. 14903635.2 filed on May 2, 2017, nine pages.
European Extended Search Report dated Oct. 14, 2015 for EP Application No. 13806313.6 filed on Jun. 20, 2013, nine pages.
European Extended Search Report dated Sep. 16, 2016 for EP Application No. 16183434.6 filed on Aug. 9, 2016, ten pages.
European Notice of Allowance dated Oct. 21, 2015 for EP Application No. 11 826 475.3, filed on Sep. 20, 2010, eight pages.
European Notice of Allowance dated Oct. 29, 2015 for EP Application No. 09 704 642.9, filed on Jan. 25, 2008, two pages.
European Office Action—Communication Pursuant to Article 94(3) EPC dated Apr. 6, 2018 for EP Application No. 15188378.2 filed on Oct. 5, 2015, four pages.
European Office Action—Communication Pursuant to Article 94(3) EPC dated Aug. 31, 2017 for EP Application No. 09739980.2 filed on Nov. 30, 2010, four pages.
European Office Action—Communication Pursuant to Article 94(3) EPC dated Mar. 9, 2016 for European Patent Application No. 09739980.2 filed May 1, 2009, five pages.
European Office Action—Communication Pursuant to Article 94(3) dated May 27, 2016 for EP Application No. 15160177.0 filed on Aug. 11, 2000, five pages.
European Office Action—Communication Pursuant to Article 94(3) dated Sep. 21, 2017 for European Application No. 16163909.1 filed on Apr. 5, 2016, three pages.
European Office Action—Communication Pursuant to Rules 70(2) and 70a(2) EPC dated May 15, 2014 in EP Application No. 09732993.2, one page.
European Office Action—Communication Pursuant to Rules 70(2) and 70a(2) EPC dated Nov. 14, 2016 in EP Application No. 16163909.1, two pages.
European Office Action—Communication Under Rule 71(3) EPC (Intention to Grant) dated Dec. 1, 2017 for European patent Application No. 09739980.2, filed on Nov. 30, 2010, seven pages.
European Office Action—Communication under Rule 71(3) EPC (Intention to Grant) dated Nov. 21, 2017 for European Patent Application No. 15160177.0, filed on Aug. 11, 2000, seven pages.
European Office Action dated Mar. 27, 2015 for EP Application No. 09 732 993.2, filed on Apr. 14, 2008, six pages.
European Opposition of European Patent No. EP1143852 lodged by Hamamatsu Photonics, Inc., Jul. 30, 2008.
European Partial Search Report dated Dec. 16, 2010 for European Application No. 10186218.3 filed on Aug. 11, 2000, seven pages.
European Partial Search Report dated Jan. 10, 2018 for EP Application No. 17171383.7 filed on May 16, 2017, eleven pages.
European Partial Search Report dated Jun. 11, 2014 for European Application No. 13178642.8, filed on May 1, 2009, five pages.
European Partial Search Report dated Jun. 28, 2016 for European Application No. 16163909.1 filed on Apr. 5, 2016, six pages.
European Summons to attend Oral Proceedings pursuant to Rule 115(1) EPC issued on Apr. 25, 2016 for European Patent Application No. 09732993.2, filed on Apr. 14, 2009, five pages.
European Summons to attend Oral Proceedings pursuant to Rule 115(1) EPC mailed on Dec. 16, 2016 for European patent application No. 15160177.0, filed on Aug. 11, 2000, seven pages.
European Supplemental Search Report dated Jul. 6, 2004 for EP Application No. 00955472.6 filed on Aug. 11, 2000, five pages.
Indian Examination Report dated Jan. 16, 2018 for Indian Application No. 2993/DELNP/2011, filed on Apr. 25, 2011, eleven pages.
Indian Examination Report dated Jul. 28, 2017 for Indian Application No. 1983/MUMNP/2007, filed on Nov. 27, 2007, seven pages.
Indian Examination Report dated Sep. 22, 2016 for Indian Application No. 7566/DELNP/2010, filed on Oct. 27, 2010, nine pages.
International Preliminary Examination Report completed on Jul. 1, 2001 for PCT/US00/22088, filed on Aug. 11, 2000, three pages.
International Preliminary Report on Patentability dated Apr. 4, 2017 for PCT Application No. PCT/CA2015/050973 filed on Sep. 28, 2015, six pages.

(56) References Cited

OTHER PUBLICATIONS

International Search Report and the Written Opinion of the International Searching Authority, or the Declaration dated Apr. 3, 2008 for PCT/US07/77892, filed on Sep. 7, 2007, ten pages.
International Search Report and Written Opinion dated Jul. 29, 2009 for PCT/US2009/043975 filed on May 14, 2009, eleven pages.
International Search Report and Written Opinion dated Oct. 24, 2017 for PCT Application No. PCT/CA2017/050564 filed on May 10, 2017, fourteen pages.
International Search Report dated Dec. 3, 2009 for PCT Patent Application No. PCT/IB2009/005700, filed on Apr. 14, 2009, three pages.
International Search Report dated Dec. 3, 2015 for PCT Application No. PCT/CA2015/050973 filed on Sep. 28, 2015, three pages.
International Search Report dated Feb. 1, 2012 for PCT Patent Application No. PCT/IB2011/002381, filed on Sep. 20, 2011, five pages.
International Search Report dated Jan. 22, 2014 for PCT Application No. PCT/IB2013/001934, filed on Jun. 20, 2013, four pages.
International Search Report dated Jul. 4, 2008 for PCT Patent Application No. PCT/US2007/080847, filed on Oct. 9, 2007, three pages.
International Search Report dated Jun. 2, 2009 for PCT Application No. PCT/EP2008/008547, filed on Oct. 9, 2008, five pages.
International Search Report dated Jun. 8, 2009 for PCT Patent Application No. PCT/CA2009/000073, filed on Jan. 23, 2009, three pages.
International Search Report dated Oct. 18, 2000 for PCT Application No. PCT/US2000/22088, filed on Aug. 11, 2000, one page.
International Search Report dated Sep. 11, 2009 for Application No. PCT/US2009/042606 filed on May 1, 2009, five pages.
Invitation to Pay Additional Fees and, Where Applicable, Protest Fee dated Jul. 4, 2017 for PCT/CA2017/050564, filed on May 10, 2017, two pages.
Japanese Final Office Action dated Feb. 5, 2018 for Japanese Patent Application No. 2016-014503, filed on Jan. 28, 2016, six pages.
Japanese First Office Action dated Feb. 1, 2016 for Japanese Patent Application No. 2015-517876 filed Jun. 20, 2013, eight pages.
Japanese First Office Action dated Jul. 28, 2017 for Japanese Patent Application No. 2016-203798 filed Oct. 17, 2016, four pages.
Japanese Notice of Allowance dated Jun. 8, 2018 for Japanese Patent Application No. 2016-203798 filed Oct. 17, 2016, six pages.
Japanese Notice of Allowance dated Sep. 16, 2016 for Japanese Patient Application No. 2015-517876 filed on Jun. 20, 2013, six pages.
Japanese Notice of Allowance dated Sep. 25, 2017 for Japanese Patent Application No. 2013-529729, filed on Mar. 21, 2013, six pages.
Japanese Office Action dated Apr. 1, 2016 for Japanese Patent Application No. 2013-529729, filed on Mar. 21, 2013, seven pages.
Japanese Office Action dated Jul. 30, 2013, issued in counterpart Japanese Application No. 2011-504574 filed on Apr. 14, 2009, six pages.
Japanese Office Action dated Mar. 3, 2017 for Japanese Patent Application No. 2016-014503, filed on Jan. 28, 2016, ten pages.
Japanese Office Action dated Mar. 19, 2018 for Japanese Application No. 2017-518785 filed on Apr. 7, 2017, eight pages.
Japanese Office Action dated Mar. 31, 2017 for Japanese Patent Application No. 2013-529729, filed on Mar. 21, 2013, eleven pages.
Japanese Office Action dated May 7, 2018 for Japanese Patent Application No. 2017-516925 filed on Mar. 28, 2017, four pages.
Japanese Office Action dated Sep. 14, 2015 for Japanese Patent Application No. 2011-504574, filed on Apr. 14, 2009, three pages.
Korean Notice of Allowance dated Apr. 27, 2017 for Korean Patent Application No. 10-2016-7007994, filed on Mar. 25, 2016, three pages.
Korean Notice of Allowance dated Apr. 29, 2016 for Korean Patent Application No. 10-2010-7024977, filed on Apr. 14, 2009, three pages.
Korean Office Action dated Apr. 17, 2018 for Korean Patent Application No. 10-2017-7012463, filed on May 8, 2017, six pages.
Korean Patent Office Action dated Jun. 25, 2014 in Korean Patent Application No. 10-2013-7035027, filed on May 14, 2009, fifteen pages.
Korean Office Action dated Nov. 30, 2015 for Korean Patent Application No. 10-2010-7024977, filed on Apr. 14, 2009, two pages.
Mexican Office Action dated May 30, 2013, issued in counterpart Mexican Application No. MX/a/2010/011249.
Novadaq Technologies Inc.'s Preliminary Response filed on Aug. 23, 2017 to Petition for Inter Partes Review of U.S. Pat. No. 8,892,190, sixty one pages.
Petition for Inter Partes Review of U.S. Pat. No. 8,892,190 (May 11, 2017), filed by Visionsense Corp., fifty four pages.
Russian Decision on Grant dated Jul. 29, 2013, issued in counterpart Russian Application No. 2011111078.14, five pages.
Russian Office Action dated Mar. 29, 2013, issued in counterpart Russian Application No. 2011111078.14, three pages.
Translation of Decision of Japanese Patent Office Trial Board revoking Counterpart Patent No. 3,881,550, twenty six pages.
U.S. Final Office Action dated Apr. 2, 2013 for U.S. Appl. No. 13/419,368, filed Mar. 13, 2012, five pages.
U.S. Final Office Action dated Apr. 4, 2017 for U.S. Appl. No. 12/933,477, filed Sep. 20, 2010, twelve pages.
U.S. Final Office Action dated Apr. 10, 2008 for U.S. Appl. No. 11/106,154, filed Apr. 14, 2005, six pages.
U.S. Final Office Action dated Apr. 12, 2017 for U.S. Appl. No. 14/543,429, filed Nov. 17, 2014, nine pages.
U.S. Final Office Action dated Apr. 20, 2016 for U.S. Appl. No. 14/543,429, filed Nov. 17, 2014, seven pages.
U.S. Final Office Action dated Aug. 10, 2012 for U.S. Appl. No. 11/912,877, filed Aug. 13, 2008, ten pages.
U.S. Final Office Action dated Dec. 4, 2014 for U.S. Appl. No. 12/776,835, filed May 10, 2010, thirteen pages.
U.S. Final Office Action dated Dec. 31, 2015 for U.S. Appl. No. 14/177,050 filed Feb. 10, 2014, eighteen pages.
U.S. Final Office Action dated Feb. 1, 2013 for U.S. Appl. No. 12/776,835, filed May 10, 2010, thirteen pages.
U.S. Final Office Action dated Feb. 4, 2015 for U.S. Appl. No. 13/314,418, filed Dec. 8, 2011, six pages.
U.S. Final Office Action dated Feb. 13, 2015 for U.S. Appl. No. 14/543,429, filed Nov. 17, 2014, six pages.
U.S. Final Office Action dated Feb. 18, 2010 for U.S. Appl. No. 11/106,154, filed Apr. 14, 2005, six pages.
U.S. Final Office Action dated Jul. 9, 2015 for U.S. Appl. No. 14/543,356, filed Nov. 17, 2014, eight pages.
U.S. Final Office Action dated Jul. 21, 2016 for U.S. Appl. No. 14/543,356, filed Nov. 17, 2014, seven pages.
U.S. Final Office Action dated Jun. 1, 2015 for U.S. Appl. No. 14/543,429, filed Nov. 17, 2014, nine pages.
U.S. Final Office Action dated Jun. 13, 2014 for U.S. Appl. No. 12/776,835, filed May 10, 2010, thirteen pages.
U.S. Final Office Action dated Jun. 25, 2014 for U.S. Appl. No. 12/933,477, filed Sep. 20, 2010, fifteen pages.
U.S. Final Office Action dated Mar. 20, 2017 for U.S. Appl. No. 14/177,050, filed Feb. 10, 2014, twenty three pages.
U.S. Final Office Action dated Mar. 28, 2013 for U.S. Appl. No. 12/063,349, filed May 12, 2010, twenty pages.
U.S. Final Office Action dated May 29, 2013 for U.S. Appl. No. 12/933,477, filed Sep. 20, 2010, twelve pages.
U.S. Final Office Action dated Nov. 6, 2013 for U.S. Appl. No. 13/419,368, filed Mar. 13, 2012, five pages.
U.S. Final Office Action dated Oct. 7, 2011 for U.S. Appl. No. 11/851,312, filed Sep. 6, 2007, ten pages.
U.S. Final Office Action dated Sep. 13, 2011 for U.S. Appl. No. 11/106,154, filed Apr. 14, 2005, five pages.
U.S. Final Office Action dated Sep. 17, 2015 for U.S. Appl. No. 12/933,477, filed Sep. 20, 2010, six pages.
U.S. Final Office Action dated Sep. 23, 2004 for U.S. Appl. No. 09/744,034, filed Apr. 27, 2001, seven pages.
U.S. Final Office Action dated Sep. 29, 2016 for U.S. Appl. No. 13/922,996, filed Jun. 20, 2013, fourteen pages.

(56) References Cited

OTHER PUBLICATIONS

U.S. Non-Final Office Action dated Apr. 1, 2015 for U.S. Appl. No. 12/933,477, filed Sep. 20, 2010, fourteen pages.
U.S. Non-Final Office Action dated Apr. 26, 2012 for U.S. Appl. No. 12/776,835, filed May 10, 2010, nine pages.
U.S. Non-Final Office Action dated Apr. 28, 2010 for U.S. Appl. No. 11/946,672, filed Nov. 28, 2007, nine pages.
U.S. Non-Final Office Action dated Aug. 10, 2016 for U.S. Appl. No. 14/177,050, filed Feb. 10, 2014, twenty pages.
U.S. Non-Final Office Action dated Aug. 29, 2014 for U.S. Appl. No. 12/063,349, filed May 12, 2010, nineteen pages.
U.S. Non-Final Office Action dated Dec. 16, 2016 for U.S. Appl. No. 14/868,369, filed Sep. 28, 2015, seven pages.
U.S. Non-Final Office Action dated Dec. 20, 2013 for U.S. Appl. No. 12/933,477, filed Sep. 20, 2010, thirteen pages.
U.S. Non-Final Office Action dated Dec. 30, 2010 for U.S. Appl. No. 11/106,154, filed Apr. 14, 2005, six pages.
U.S. Non-Final Office Action dated Feb. 1, 2011 for U.S. Appl. No. 11/851,312, filed Sep. 6, 2007, seven pages.
U.S. Non-Final Office Action dated Feb. 5, 2016 for U.S. Appl. No. 14/543,356, filed Nov. 17, 2014, seven pages.
U.S. Non-Final Office Action dated Jan. 8, 2018 for U.S. Appl. No. 15/077,677, filed Mar. 22, 2016, nine pages.
U.S. Non-Final Office Action dated Jan. 9, 2009 for U.S. Appl. No. 11/106,154, filed Apr. 14, 2005, six pages.
U.S. Non-Final Office Action dated Jan. 22, 2014 for U.S. Appl. No. 11/851,312, filed Sep. 6, 2007, ten pages.
U.S. Non-Final Office Action dated Jan. 27, 2012 for U.S. Appl. No. 11/912,877, filed Aug. 13, 2008, eleven pages.
U.S. Non-Final Office Action dated Jan. 31, 2018 for U.S. Appl. No. 15/799,727 filed Oct. 31, 2017, seven pages.
U.S. Non-Final Office Action dated Jul. 2, 2015 for U.S. Appl. No. 14/177,050, filed Feb. 10, 2014, nineteen pages.
U.S. Non-Final Office Action dated Jul. 8, 2014 for U.S. Appl. No. 13/314,418, filed Dec. 8, 2011, seven pages.
U.S. Non-Final Office Action dated Jul. 22, 2015 for U.S. Appl. No. 13/314,418, filed Dec. 8, 2011, six pages.
U.S. Non-Final Office Action dated Jun. 28, 2012 for U.S. Appl. No. 12/063,349, filed May 12, 2010, seventeen pages.
U.S. Non-Final Office Action dated Mar. 6, 2007 for U.S. Appl. No. 11/106,154, filed Apr. 14, 2005, eight pages.
U.S. Non-Final Office Action dated Mar. 10, 2004 for U.S. Appl. No. 09/744,034, filed Apr. 27, 2001, seven pages.
U.S. Non-Final Office Action dated Mar. 13, 2015 for U.S. Appl. No. 14/543,356, filed Nov. 17, 2014, eight pages.
U.S. Non-Final Office Action dated Mar. 22, 2018 for U.S. Appl. No. 15/610,102, filed May 31, 2017, eleven pages.
U.S. Non-Final Office Action dated May 6, 2015 for U.S. Appl. No. 12/063,349, filed May 12, 2010, seventeen pages.
U.S. Non-Final Office Action dated May 21, 2015 for U.S. Appl. No. 13/922,996, filed Jun. 20, 2013, fourteen pages.
U.S. Non-Final Office Action dated Nov. 9, 2015 for U.S. Appl. No. 14/177,045, filed Feb. 10, 2014, seven pages.
U.S. Non-Final Office Action dated Nov. 18, 2016 for U.S. Appl. No. 12/933,477, filed Sep. 20, 2010, six pages.
U.S. Non-Final Office Action dated Nov. 27, 2015 for U.S. Appl. No. 14/543,429, filed Nov. 17, 2014, six pages.
U.S. Non-Final Office Action dated Oct. 3, 2013 for U.S. Appl. No. 12/776,835, filed May 10, 2010, twelve pages.
U.S. Non-Final Office Action dated Oct. 12, 2016 for U.S. Appl. No. 14/543,429, filed Nov. 17, 2014, nine pages.
U.S. Non-Final Office Action dated Oct. 13, 2017 for U.S. Appl. No. 13/922,996, filed Jun. 20, 2013, seventeen pages.
U.S. Non-Final Office Action dated Oct. 26, 2017 for U.S. Appl. No. 14/543,429, filed Nov. 17, 2014, nine pages.
U.S. Non-Final Office Action dated Oct. 28, 2016 for U.S. Appl. No. 14/543,356, filed Nov. 17, 2014, eight pages.
U.S. Non-Final Office Action dated Sep. 5, 2012 for U.S. Appl. No. 12/933,477, filed Sep. 20, 2010, seven pages.
U.S. Non-Final Office Action dated Sep. 15, 2010 for U.S. Appl. No. 11/106,154, filed Apr. 14, 2005, six pages.
U.S. Non-Final Office Action dated Sep. 27, 2017 for U.S. Appl. No. 14/177,050, filed Feb. 10, 2014, twenty two pages.
U.S. Notice of Allowance dated Apr. 17, 2014 for U.S. Appl. No. 13/419,368, filed Mar. 13, 2012, five pages.
U.S. Notice of Allowance dated Aug. 7, 2014 for U.S. Appl. No. 13/850,063, filed Mar. 25, 2013, nine pages.
U.S. Notice of Allowance dated Dec. 2, 2016 for U.S. Appl. No. 14/598,832, filed Jan. 16, 2015, seven pages.
U.S. Notice of Allowance dated Dec. 6, 2017 for U.S. Appl. No. 15/476,290, filed Mar. 31, 2017, nine pages.
U.S. Notice of Allowance dated Jul. 12, 2017 for U.S. Appl. No. 14/868,369, filed Sep. 28, 2015, nine pages.
U.S. Notice of Allowance dated Jul. 13, 2016 for U.S. Appl. No. 14/598,832, filed Jan. 16, 2015, seven pages.
U.S. Notice of Allowance dated Mar. 7, 2005 for U.S. Appl. No. 09/744,034, filed Apr. 27, 2001, five pages.
U.S. Notice of Allowance dated Mar. 15, 2016 for U.S. Appl. No. 14/598,832, filed Jan. 16, 2015, seven pages.
U.S. Notice of Allowance dated Mar. 29, 2018 for U.S. Appl. No. 14/177,050, filed Feb. 10, 2014, ten pages.
U.S. Notice of Allowance dated May 26, 2016 for U.S. Appl. No. 14/177,045, filed Feb. 10, 2014, eight pages.
U.S. Notice of Allowance dated Nov. 25, 2015 for U.S. Appl. No. 14/598,832, filed Jan. 16, 2015, seven pages.
U.S. Notice of Allowance dated Nov. 30, 2010 for U.S. Appl. No. 11/946,672, filed Nov. 28, 2007, six pages.
U.S. Notice of Allowance dated Oct. 4, 2013 for U.S. Appl. No. 11/912,877, filed Aug. 13, 2008, nine pages.
U.S. Notice of Allowance dated Oct. 6, 2014 for U.S. Appl. No. 13/419,368, filed Mar. 13, 2012, five pages.
U.S. Notice of Allowance dated Oct. 16, 2014 for U.S. Appl. No. 13/850,063, filed Mar. 25, 2013, eight pages.
U.S. Notice of Allowance dated Oct. 18, 2012 for U.S. Appl. No. 12/841,659, filed Jul. 22, 2010, seven pages.
U.S. Notice of Allowance dated Sep. 6, 2018 for U.S. Appl. No. 12/776,835, filed May 10, 2010, five pages.
U.S. Notice of Allowance dated Sep. 6, 2018 for U.S. Appl. No. 13/922,996, filed Jun. 20, 2013, nine pages.
U.S. Notice of Allowance dated Sep. 11, 2018 for U.S. Appl. No. 15/799,727, filed Oct. 31, 2017, eight pages.
U.S. Restriction Requirement dated Jun. 26, 2017 for U.S. Appl. No. 15/077,677, filed Mar. 22, 2016, seven pages.
Written Opinion of the International Searching Authority dated Jul. 4, 2008 for PCT Patent Application No. PCT/US2007/080847, filed on Oct. 9, 2007, six pages.
Written Opinion of the International Searching Authority dated Jun. 2, 2009 for PCT Patent Application No. PCT/EP2008/008547, filed on Oct. 9, 2008, eleven pages.
Written Opinion of the International Searching Authority dated Dec. 3, 2009 for PCT Patent Application No. PCT/IB2009/005700, filed on Apr. 14, 2009, six pages.
Written Opinion of the International Searching Authority dated Dec. 3, 2015 for PCT Patent Application No. PCT/CA2015/050973 filed on Sep. 28, 2015, five pages.
Written Opinion of the International Searching Authority dated Feb. 1, 2012 for PCT Patent Application No. PCT/IB2011/002381, filed on Sep. 20, 2011, four pages.
Written Opinion of the International Searching Authority dated Jan. 22, 2014 for PCT Patent Application No. PCT/IB2013/001934, filed on Jun. 20, 2013, six pages.
Written Opinion of the International Searching Authority dated Jun. 8, 2009 for PCT Patent Application No. PCT/CA2009/000073, filed on Jan. 23, 2009, four pages.

* cited by examiner

NIR imaging of cavernous nerves

NIRF - penile crura and cavernous nerves

INTRAOPERATIVE DETERMINATION OF NERVE LOCATION

CROSS-REFERENCES TO RELATED APPLICATIONS

This application claims priority from and the benefit of U.S. Provisional Application 60/713,643, filed Sep. 2, 2005. The contents of which are hereby incorporated by reference.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK.

Not Applicable

BACKGROUND OF THE INVENTION

A variety of medical techniques suitable for imaging biological tissues and organs are known. These include traditional x-rays, ultra-sound, magnetic resonance imaging, and computerized tomography.

A variety of dyes useful for medical imaging have been described, including radio opaque dyes, fluorescent dyes, and calorimetric dyes (see e.g., U.S. Pat. Nos. 5,699,798; 5,279,298; 6,351,663). Imaging techniques and systems using fluorescent dyes have been described for the heart and eye (see, e.g., U.S. Pat. No. 5,279,298). Some dyes can serve both an imaging function and a therapeutic function (see, e.g. U. S. Pat. No. 6,840,933). Some specific neuronal imaging agents have been used to visualize tissue in the central nervous system. Tracer uptake and transport has been demonstrated in different studies using various routes of administration including antegrade, retrograde and combined routes (Jones et al. 1978, Annu Rev Neurosci.; 1:215; Rosina A., 1982, Neurosci Lett. 33(3):217; Illing RB, et al., 1985, Neuroscience 14(2):455; Sloniewski P, et al., 1985, Neurosci Lett. 60(2):189; and Schmued et al., 1986, Brain Res. 377(1):147). After appropriate time for endo/pinocytosis, perineural lymphatic and axonal transport, which generally measures 0.5-2 mm per hour, tracers were visually detected using ultraviolet or visible light (Bentivoglio et al., 1980, Neurosci Lett. 18(1):19; Minciacchi D et al., 1991, J Neurosci Methods. 38(2-3):183). Non-toxic tracers such as Indocyanine Green, Fast Blue, and Fluorogold, have been used in mammals without evidence of neuronal toxicity several months after the treatment (Thielert et al., 1993, J Comp Neurol. 337(1):113; Yeterian et al., 1994, Exp Brain Res. 99(3):383; vogt Weisenhorn et al., 1995, J Comp Neurol. 362(2):233). Marangos et al. labeled the auditory nerve using Fluorogold and Fast Blue in rats and monkeys by suctioning out perilymph and filling the cochlea with neuronal tracers to identify the nerve and cochlear brain stem nucleus for the positioning of electrodes for an auditory neuroprosthesis (Marangos N, et al., 2001, Hear Res. 162 (1-2):48).

The prostate is an accessory sex gland in men. It is about the size of a walnut, and surrounds the neck of the bladder and the urethra, the tube that carries urine from the bladder. It is partly muscular and partly glandular, with ducts opening into the prostatic portion of the urethra. It is made up of three lobes: a center lobe with one lobe on each side. The prostate gland secretes a slightly alkaline fluid that forms part of the seminal fluid.

Prostate cancer is the most common type of cancer (excluding skin cancer) among American men. It is found most often in men aged 50 and over, with an especially high prevalence rate among African Americans. In men, it is second only to lung cancer as a cause of cancer-related death. The American Cancer Society has estimated that 220,900 new cases of prostate cancer will be diagnosed annually and that 28,900 men annually will die of the disease (Cancer Facts and Figures, American Cancer Society, 2003). Treatment options include hormonal therapy aimed at lowering testosterone levels, radiation therapy, chemo therapy and surgery.

Surgical removal of the entire prostate gland is called radical prostatectomy ("RP"). The aim of radical prostatectomy is removal of early-stage prostate cancer, one that has not yet spread locally or to distant organs. Radical prostatectomy complications include incontinence and impotence. Most men experience urinary incontinence after surgery. Many continue to have intermittent problems with dribbling caused by coughing or exertion. Damage to nerves which innervate both the prostate and the penis plays a significant part in these unwanted side effects. Approximately 40 to 60% of men undergoing RP are impotent due to injury to the cavernous nerves during the surgery.

Topographically, cavernous nerves are part of the neurovascular bundle, which travels at the posterolateral border of the prostate, outside the prostatic capsule and on the anterolateral surface of the rectum. McNeal described large superior and small inferior pedicles innervating the base and the apex of the prostate respectively (McNeal J E., 1988, Am J Surg Pathol.; 12(8):619.). After reaching the apex at the 5 and 7-o'clock positions, nerves travel posterolaterally to the urethra. At the level of membranous urethra they divide into more superficial branches to the sphincter muscle and finally at the level of the hilum of the penis, together with the arteries, the nerves pierce the cavernous bodies and innervate erectile tissue diffusely (Lue et al., 1983, J Urol.; 130(6):1237; Breza et al., 1989, J Urol. 141(2):437).

The risk of impotence may be reduced by avoiding cutting or stretching bundles of nerves and blood vessels that run along the surface of the prostate gland and are needed for an erection. Successful nerve sparing surgery, however, is often difficult to achieve because of the difficulty in distinguishing between the prostate tissue, in particular the cancerous prostate tissue, and the innervating nerve tissue. Appropriate mapping of the nerves can also lead to better understanding of cavernous nerves topography and penile accessory innervation. Accordingly, a need exists for improved methods of imaging peripheral nerves, such as the nerves which innervate the prostate. The present invention fills these and other needs.

BRIEF SUMMARY OF THE INVENTION

The invention provides methods of determining the location of a nerve or portion of a nerve of interest in a subject during a surgical operation. The methods comprise, prior to the surgical operation, administering to an organ or area of the subject innervated by the nerve or portion of a nerve of interest a dye which fluoresces at an emission wavelength when the dye is contacted with an excitation wavelength, whereby the dye is taken up by or proceeds along the path of the nerve; exposing the nerve or portion of nerve during said operation to illumination comprising said excitation wavelength, thereby causing the fluorescent dye in or along the nerve or portion thereof to fluoresce; and detecting the fluorescence of the dye, thereby determining the location of said nerve or portion of nerve during said surgical operation. In some embodiments, the dye is injected into a cavernous body of the penis. In some embodiments, the injection into the cavernous body is into a crus of said cavernous body. In some embodiments, said dye is injected into a cavernous body of the clitoris, into the vaginal wall, or into both. In some embodiments, the dye is injected by epidural injection. In some embodiments, the nerve is transected during the surgical operation, creating two ends, and the detection of fluorescence of step is used to determine the location of the two ends. In some embodiments, the determination of the location of the two ends of the transected nerve is used to guide grafting of nerve tissue between the ends or to reconnect them. In some embodiments, the determination of the location of the nerve is used to avoid transecting said nerve. In some embodiments, the surgical operation is a radical prostatectomy. In some embodiments, the surgical operation is a radical hysterectomy. In some embodiments, the nerve is a cavernous nerve. In some embodiments, the nerve or aid portion of the nerve is visualized on a image display, thereby permitting determination of the location of the nerve or portion of the nerve. In some embodiments, the exposing of the nerve or portion of nerve to excitation wavelength is by a laparoscopic instrument. In some embodiments, the dye is a dye which fluoresces when exposed to near infrared light. In some embodiments, the dye is a tricarbocyanine dye or an analog thereof. In some embodiments, the tricarbocyanine dye is indocyanine green. In some embodiments, the subject is a human. In some embodiments, the dye is administered between 1 hour and 30 hours before the surgical operation. In some embodiments, the dye is administered between about 18 hours and about 24 hours before the surgical operation. In some embodiments, the dye is administered between about 6 hours and about 24 hours before the surgical operation. In some embodiments, the nerve is the small cavernous nerve. In some embodiments, the nerve is the large cavernous nerve.

BRIEF DESCRIPTION OF THE DRAWINGS

FIG. 1a shows the exposing of the penis of a rat. FIGS. 1b and 1c show the injection of ICG into the crura of the left and right cavernous bodies, respectively. FIG. 1d shows the exposed penile crura and cavernous nerves under near infrared (NIRF) illumination following injection of ICG. Arrows show the location of the cavernous nerves.

FIG. 2 shows a cavernous nerve under NIRF illumination following injection of ICG into the crura of the cavernous bodies. The white arrow points to the nerve.

FIG. 3 shows a hook electrode (arrow) hooked around a cavernous nerve under NIRF illumination, after ICG injection into the crura of the cavernous bodies.

FIG. 4 shows NIRF illumination of a cavernous nerve (arrow) from an animal injected with ICG as described above.

FIGS. 5a and 5b are photographs of a cavernous nerve excised from an animal whose penile crura were injected with ICG. FIG. 5a shows the nerve under infrared and LED illumination. FIG. 5b shows the same nerve under NIRF alone.

DETAILED DESCRIPTION OF THE INVENTION

Figure 1A:
FIGS. 1a-d.
Figure 1B:
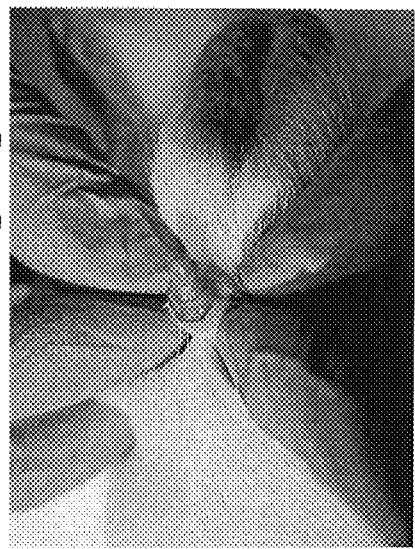
Figure 1C:
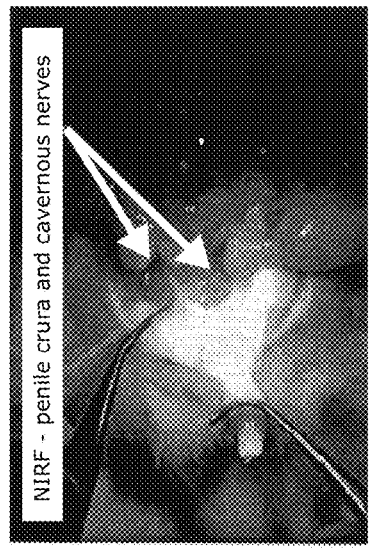

As set forth in the Background, some dyes and other agents have been used to image nerve cells in the eye and nerves connecting the ear to the central nervous system. Surprisingly, dyes can also be used to image (that is, to permit visualization) of nerves elsewhere in the body and can be used either to reduce the chance that nerves will inadvertently be transected during surgical procedures or to help guide neural grafts when unintended transactions occur or when they cannot otherwise be avoided.

The original surgical treatment for prostate cancer was radical perineal prostatectomy, which was followed, in the 1940's, by radical retropubic prostatectomy. Both forms of surgery not only typically led to incontinence and to impotence, but also resulted in extensive bleeding, which made it difficult to detect and preserve associated structures. The severity of the side effects from these surgical procedures made radiation therapy for prostate cancer a popular alternative once it was developed in the 1960's. The development of less bloody surgical techniques in the 1970's, however, resulted in the preservation of more structure and less inadvertent damage to blood vessels and to nerves. In the early 1980's, Drs. Patrick Walsh and Pieter Donker were able for the first time to determine that the nerves for the penis did not go through the prostate. In 1982, Dr. Walsh showed it was possible to remove the prostate without severing the nerves innervating the penis. This so-called "nerve sparing" surgery, medically termed "anatomic radical prostatectomy," properly done, permits retention of potency in many patients. Nonetheless, surgeons still sever the nerves in some patients, leading to loss of potency in those patients. Thus, visualizing the nerves during surgery is highly desirable.

In particular, the methods of the invention provide for the visualization of cavernous nerve cells during radical prostatectomy ("RP") and other surgical procedures. The recovery of erectile function is a significant concern for patients undergoing treatment for localized prostate cancer. As noted in the Background, impotence is a common side effect of RP resulting from damage to the cavernous nerves that innervate the penis. Damage to the nerve tissue surrounding the prostate usually results from the surgeon's inability to distinguish between prostate tissue and nerve tissue. The present invention increases the ability of the surgeon to identify and avoid the cavernous nerves as they traverse the area surrounding the prostate and other abdominal organs and thus to reduce or to prevent damage to those nerves tissue during the course of surgery.

The methods are useful not only to reduce the inadvertent transection of these nerves during prostate surgery, but also to aid in grafting the ends of the nerves if they are transected. In the event of transection, genitofemoral or sural nerve grafts can be applied directly to the ends to facilitate sprouting of regenerative neural fibers. In this case, the light visible from the fluorescence of the ends of transected nerves provides a target to guide the anastomosis of the nerves by the nerve graft. The methods can further be used to identify the cavernous nerves in patients undergoing radical pelvic surgeries, such as low anterior resection or abdominal perineal resection.

In the methods of the invention, a fluorescent dye that can be taken up by nerve cells and that has low toxicity is injected into the corpora cavernosa or one corpus cavernosum of the penis (as persons of skill are aware, "corpora cavernosa" is the plural form and "corpus cavernosum" is the singular form. Thus, the practitioner may choose to inject the dye into one corpus cavernosum or into both, depending on whether the practitioner wishes to be able to image one or both of the subject's cavernous nerves.) For convenience, the corpora cavernosa will sometimes be referred to herein as the "cavernous bodies."

The injections may be made into the cavernous bodies as they run parallel to each other along the length of the penis, or at the base or root of the penis into the crura, which is the area where the two corpora cavernosa diverge within the subject's body and anchor to bone. (If the intent is to visualize just one of the cavernous nerves, the injection will be made into the appropriate crus of penis, "crus" being the singular form of "crura.") In studies underlying the present invention, injections into the cavernous bodies closer to the glans of the penis, and therefore more distal from the body, resulted in less favorable visualization of the nerves than did injections into the crura. Accordingly, injection into the crura is preferred.

In humans, the injections are easily made by palpating the pubic bone and making the injection about 1 cm distal (along the penis, away from the body) from the pubic bone. This location is the same as that at which patients are taught to self inject erectile dysfunction drugs to cause erections, so it is well known and relatively easy to find even for the layperson.

Following injection, the dye is transported along the nerves supplying the organ, permitting visualization of the nerve and determination of their location. Without wishing to be bound by theory, it is surmised that at least some of the flow of the dye is in lymphatic channels around the nerve rather than in the nerve itself. This belief arises because, in studies underlying the invention, it was noted both that the periphery of the nerve fluoresced more strongly than the middle of the nerve that the speed at which the dye moved along the nerve seemed faster than might be expected from retrograde transport alone.

Since there are two sets of cavernous nerves, which run on the left and right sides of the prostate, the surgeon will generally choose to inject the dye into both the left and the right cavernous bodies of the penis so that both sets of nerves can be visualized. The dye is then transported along by the cavernous nerves. Helpfully, accessory nerves may also be visualized by this procedure. Since these nerves can also play some role in achieving erections, the visualization of these nerves and consequent ability to avoid transecting them, or to reconnect them if they are transected, further improves the prospect that the patient will not be impotent following the operation.

In some instances, which are expected to be relatively uncommon, the surgeon may wish to visualize only one cavernous nerve. In these instances, the surgeon may inject dye only into the cavernous body innervated by the cavernous nerve whose visualization is desired. It is contemplated, however, that the surgeon will usually want the ability to visualize and thereby locate, the nerves around both sides of the prostate, in part because visualizing the transected ends will permit the nerves to be bridged (interpositioned) with genitofemoral or sural nerve. Additionally, in some prostate cancers, it is difficult for the surgeon to determine where the prostate tissue ends. In such cases, visualization of the nerves through the methods of the invention will assist the surgeon determine the margin between prostate and non-prostate tissue. Accordingly, injection of dye into both cavernous bodies is preferred.

Imaging of the nerves can also be made by injecting the dye by an epidural injection in the area of S2-S4 of the spinal cord level to allow antegrade flow of the dye along the nerve. Tens of thousands of epidural injections are made every year, for example, to women undergoing childbirth, and techniques for making such injections, and for positioning them at desired levels are well known in the art. It is expected that dye injected by epidural injection, will undergo transport along the nerves from the spine towards the penis, and will permit visualization of the nerves in a manner like that seen from injections of dye into the cavernous bodies.

In recent years, it has also been recognized that women undergoing gynecological operations, such as hysterectomies, can suffer damage to nerves controlling vaginal erectile tissue in a manner similar to that sustained by men under radical prostatectomy. Nerve damage in the course of radical hysterectomies can also result in post-operative bladder dysfunction due to damage to the pelvic autonomic nerves during surgical resection, as well as other pelvic morbidity. This recognition has led to attempts to develop nerve-sparing techniques for gynecological procedures. See, e.g., Possover, Gynecol Oncol. 2003; 90(2):245-7; Ito and Saito, Eur J Surg Oncol. (2004), 30(10):1137-40; Butler-Manuel et al., (2000), Cancer, 89(4):834-841; Trimbos et al., Int J Gynecol Cancer (2001), 11:180-186.

Based on the results seen in visualizing the cavernous nerves in male animals, it is expected that the same procedures can be used to visualize the nerves innervating homologous structures in women, thereby improving the ability to visualize and locate the nerves during gynecological operations, such as simple and radical hysterectomies. The clitoris contains a glans, shaft, and crura containing cavernous bodies homologous to the structures of the penis. The dye can be injected into the cavernous bodies in the clitoris in a like manner to the injections described above with regard to the penis. Specifically, the dye is injected into the clitoris or into the anterior wall of the vagina just below the clitoris or, preferably, both. Alternatively, or in addition, the dye is administered as an epidural injection at the S2-S4 spinal cord level, at the start of the parasympathetic outflow. It is expected that the improved ability to visualize the nerves will help the surgeon avoid transecting the nerves or, if the nerves are transected, will help the surgeon identify the cut ends and assist in bridging the gap with a nerve graft or, where possible, reattaching the cut ends.

Based on the results seen in visualizing the cavernous nerves following injection of dye into the tissue of the organ that they innervate, it is believed that injection of dye into the tissue of other organs will result in the uptake of dye by nerves innervating those organs and will result in the ability to image those nerves. It is not expected, however, that this method will be useful in imaging the brain.

It is understood that fluorescent dyes have a particular excitation wavelength which causes the dye to fluoresce and emit light of a particular emission wavelength. As persons of skill are aware, there is a considerable literature on the characteristics of different dyes, including their excitation wavelength and emission wavelength.

The methods described herein are suitable for use in mammals. Examples of mammals for which the techniques can be used include, but are not limited to, non-human primates, dogs, cats, sheep, cows, pigs, horses, mice, rats, rabbits, and guinea pigs. The methods are particularly useful in visualizing nerves in humans, and particularly the cavernous nerves in humans.

Penile Anatomy

It is assumed that urologic surgeons and other persons of skill are well familiar with the anatomy of the penis, the prostate, and the surrounding areas, and that no detailed discussion is needed here. For purposes of the present discussion, it is noted that the penis can be thought of as comprising three cylinders. Two, the corpora cavernosa, are disposed on either side of the penis, and make up the bulk of the penis. The third, the corpus spongiosum, which contains the urethra, is disposed in the middle of the penis, in a cleft between the undersides of the corpora cavernosa. A "deep artery" runs down the center of each corpus cavernosum and provides blood to sinusoidal spaces in the respective corpus. During erection, the deep artery is expanded and the sinusoidal spaces are swollen, while the emissary veins that drain blood from the corpora cavernosa are compressed. The sinusoidal spaces within each corpus cavernosum communicate, permitting a common intracavernosal pressure and a common penile rigidity.

Preganglionic parasympathetic neurons originate from the sacral spinal nucleus at levels S2-S4. The axons travel from the anterior sacral roots and end as cavernous nerves giving innervation to the cavernous bodies. Stimulation of pelvic and cavernous nerves has been shown to result in an erection in animals as well as in humans. Complete loss of erection is observed after bilateral cavernous nerve resection. The sympathetic contribution to the cavernous bodies originates at the T11-L2 level of the spinal cord, and travels through the prevertebral pathway, consisting of lumbar splanchnic nerves, hypogastric nerves, pelvic plexus and cavernous nerves and through the paravertebral chain, leading to the pelvic nerves, pelvic plexus, cavernous and pudendal nerves.

Stimulation of the paravertebral sympathetic chain results in detumescence. Topographically, cavernous nerves are part of the neurovascular bundle, which travels at the posterolateral border of the prostate, outside the prostatic capsule and on the anterolateral surface of the rectum. Large superior and small inferior pedicles innervate the base and the apex of the prostate, respectively. After reaching the apex at the 5 and 7 o'clock positions, nerves travel posterolaterally to the urethra. At the level of membranous urethra, they divide into more superficial branches to the sphincter muscle and finally at the level of the hilum of the penis, together with the arteries, the nerves pierce the cavernous bodies and innervate erectile tissue diffusely. A description of the prostatic plexus and associated nerves, including the cavernous nerves, can be found on-line by entering "http://" followed by "education.yahoo.com/reference/gray/subjects/subject?id=220".

Instrumentation

For convenience, the following discussion will refer to instrumentation optimized for use with the exemplar dye ICG. Persons of skill are, of course, aware of the excitation and emission frequencies of other fluorescent dyes and can adjust the device as needed for use with respect to other dyes as desired.

Conveniently, the device used for visualization of the nerves in the area of interest comprises both a laser and a camera. For use with ICG, the laser preferably consists of a laser diode providing a maximum of 3W output at 806 nm. For other dyes, the laser diode is selected to provide a light with a wavelength at an excitation frequency appropriate for the dye selected. For convenience of reference, the discussion below refers to the exemplar dye ICG. Persons of skill will recognize that the other dyes mentioned herein as suitable for use in the inventive methods and procedures could be substituted for ICG, with the light source selected or adjusted to provide illumination optimized for the excitation frequency suitable for the particular dye chosen and the device for capturing the light emitted by the dye being selected or adjusted to be able to receive light of the appropriate frequency.

The laser output is decollimated (i.e. optics are used to spread out the laser light from a tight beam) to provide even illumination over a field of view, for example, 7.6 cm by 7.6 cm at a working distance of 30 cm. The unit typically contains a charge-coupled device ("CCD") video camera sensitive into the near infrared spectrum and, for use with ICG, is equipped with an 815 nm edge filter. An articulated arm, connected to a wheeled base, supports the laser/camera device. This allows the imaging head to be moved into close proximity to the surgical table and for vertical movement of the head to attain the correct focal distance above the area of interest. The imaging head and extension arm that protrudes over the surgical field is typically covered with an optically transparent sterile drape. The laser can be activated by means of a computer command or by foot pedal. Such laser/camera devices are commercially available. Laser/camera devices suitable for intra-operative imaging are commercially available. In a preferred embodiment, the laser/camera device is a SPY® Intra-operative Imaging System (Novadaq Technologies, Inc., Mississauga, Ontario, Canada).

For visualizing the cavernous nerves, the ICG is administered by injection into one of the corpus cavernosum of interest, preferably into the crus, permitting the dye to be taken up by the nerve serving that corpus cavernosum, and transported by retrograde transport back towards the pelvic plexus. Generally, the practitioner will want to visualize both cavernous nerves and will inject the dye into both cavernous bodies. Following an interval sufficient for the dye to be transported throughout the area in which the nerve is to be visualized, a 806 nm excitation light causes the dye to fluoresce, emitting light at 830 nm. The emitted light can then be imaged directly or, preferably, is captured using an imaging system. Typically, the capture system is a charge-coupled device (CCD) camera or CMOS (complementary symmetry metal oxide semiconductor) image sensor, which feeds the image to a monitor so that the surgeon can visualize the fluorescence of the dye in the nerves in the area of interest in real time. Optionally, the camera is also attached to a computer and the image is saved, which not only permits documentation of the nerve's location and path in the area of interest, but also can be used for training urologic surgeons, nurses, and other medical staff. Typically, the time required for positioning the device is 2 minutes, while the total time that the nerve or nerves are illuminated with laser light is 30 seconds.

The methods described herein are suitable for use in mammals. Examples of suitable mammals include, but are not limited to, humans, non-human primates, dogs, cats, sheep, cows, pigs, horses, mice, rats, rabbits, and guinea pigs. Use in humans is primates, and particularly in humans, is preferred.

Dyes for imaging

As persons of skill are aware, fluorescent dyes have a particular excitation wavelength which causes the dye to fluoresce and emit light of a particular emission wavelength. Persons of skill will appreciate that a considerable literature is available in the art on the characteristics of different dyes, including their excitation wavelength and emission wavelength. This literature is well known, and will not be set forth in detail herein.

The dye is imaged by exciting it with a light that has an excitation wavelength appropriate for the particular dye used. Persons of skill are aware that a variety of dyes exist, and that each dye has an excitation wavelength and an emission wavelength. Some dyes, for example, fluoresce under ultraviolet ("UV") illumination while others fluoresce under incandescent illumination. There is a large literature on the use of fluorescent dyes and probes in biological assays, such as Dewey, T. G., Ed., Biophysical and Biochemical Aspects of Fluorescence Spectroscopy, Plenum Publishing (1991), Guilbault, G. G., Ed., Practical Fluorescence, Second Edition, Marcel Dekker (1990), Lakowicz, J. R., Ed., Topics in Fluorescence Spectroscopy: Techniques (Volume 1, 1991); Principles (Volume 2, 1991); Biochemical Applications (Volume 3, 1992); Probe Design and Chemical Sensing (Volume 4, 1994); Nonlinear and Two-Photon Induced Fluorescence (Volume 5, 1997); Protein Fluorescence (Volume 6, 2000); DNA Technology (Volume 7, 2003); Plenum Publishing, and Lakowicz, J. R., Principles of Fluorescence Spectroscopy, Second Edition, Plenum Publishing (1999). Invitrogen Inc. (Carlsbad, Calif.) makes a comprehensive handbook on fluorescence and its use in biological assays available on its website. The reference is entitled "The Handbook—A Guide to Fluorescent Probes and Labeling Technologies" and is currently in its tenth edition. The Handbook can be found on-line by entering "http://H" followed by "probes.invitrogen.com/handbook/".

Fluorescent dyes suitable for use in the methods of the invention are non-toxic dyes which fluoresce when exposed to radiant energy, e.g. light. Preferably, the dyes are near infrared fluorochromes, or "NIRF" that emit light in the near infra red spectrum. In some embodiments, the dye is a tricarbocyanine dye, and in particularly preferred embodiments, is indocyanine green ("ICG"). ICG is commercially available from, for example, Akom, Inc. (Buffalo Grove, Ill.), which sells it under the name IC-GREEN™. In other embodiments the dye is selected from fluorescein isothiocyanate, rhodamine, phycoerythrin, phycocyanin, allophycocyanin, o-phthaldehyde, fluorescamine, Rose Bengal, trypan blue, and fluoro-gold. The dyes may be mixed or combined. In some embodiments, dye analogs may be used. A "dye analog" is a dye that has been chemically modified, but still retains its ability to fluoresce when exposed to radiant energy of an appropriate wavelength. ICG, Fast Blue and Fluorogold have all been used in mammals with low evidence of neuronal toxicity and are preferred.

ICG is particularly preferred both because it has low toxicity and because it has been approved by the Food and Drug Administration for several diagnostic purposes in humans. Its absorption (excitation) and emission peaks (805 and 835 nm, respectively) lie within the "optical window" of tissue, where absorption due to endogenous chromophores is low. Near infrared light can therefore penetrate tissue to a depth of several millimeters to a few centimeters. After intravenous injection, ICG is bound within 1 to 2 seconds, mainly to globulins (1-lipoproteins), and remains intravascular, with normal vascular permeability. ICG is not metabolized in the body and is excreted exclusively by the liver, with a plasma half-life of 3 to 4 minutes. It is not reabsorbed from the intestine and does not undergo enterohepatic recirculation. Commercially available ICG contains iodine and should not be administered to persons with a history of reaction to iodine. The recommended dose for ICG video angiography is 0.2 to 0.5 mg/kg; the maximum daily dose should not exceed 5 mg/kg.

For intraoperatively visualizing the cavernous nerves, the surgical field, or the portion of the surgical field in which imaging is desired, is illuminated with a light of the excitation wavelength or wavelengths suitable for the dye or dyes used. Since the nerves are quite thin (accounting in part for the difficulty in discerning them with the unaided eye), ambient light may need to be dimmed to permit the fluorescence to be seen. Observation will typically also require magnification. Where the excitation wavelength is outside of the visible range (where, for example, the excitation wavelength is in the ultraviolet or near infrared range), the light source may be designed to permit switching or "toggling" between the excitation wavelength and visible light. This permits the practitioner to note the position of the nerves using the fluorescent property in relation to the rest of the surgical field and surrounding (but non-fluorescent) structures.

In some embodiments, an instrument having an optical configuration similar to a fluorescence microscope may be used, in which a dichroic mirror is used to split the paths of the illumination (the excitation light). The excitation light reflects off the surface of the dichroic mirror into the objective, while the fluorescence emission passes through the dichroic mirror to the eyepiece or is converted into a signal to be presented on a screen. The instrument may further have an excitation filter or an emission filter, or both, to select the wavelengths appropriate for each function. Conveniently, the filters are interference filters, which block transmission of frequencies out of their bandpass.

The dye is typically administered by an injection into one or both of the corpora cavemosa. Typically, the dye will be administered some hours preoperatively, to permit the dye to be taken up by the nerves and transported throughout the area of interest prior to commencing the radical prostatectomy or other surgical operation.

Conveniently, the dye may be administered in the patient's room. Typically, the dye is administered sufficiently before the intended surgery to permit the nerves to take up the dye and to transport it over the length of their axons, but not so long before the surgery that the dye has been transported in large part to the cell body. Preferably, the dye is administered more than 2 hours, but less than 48 hours, before the intended surgery. More preferably, the dye is administered at least about 5 hours but not more than 40 hours before the intended surgery. In some embodiments, the dye is administered at least about 10 hours but not more than 36 hours before the intended surgery. In other embodiments, the dye is administered at least about 14 hours but not more than 30 hours before the intended surgery. In preferred embodiments, the dye is administered between about 16 hours to 26 hours before the intended surgery. In still preferred embodiments, the dye is administered between about 18 hours to about 24 hours before the intended surgery, with "about" meaning an hour on either side.

The maximum daily dosage of ICG for adults is 2 mg/kg. There is no data available describing the signs, symptoms, or laboratory findings accompanying an overdose of ICG. The $LD_{50}$ after IV administration ranges between 60 and 80 mg/kg in mice, 50 and 70 mg/kg in rats, and 50 to 80 mg/kg in rabbits.

EXAMPLES

Example 1

Intraoperative video angiography is performed with a laser-fluorescence imaging device (Novadaq Technologies, Inc., Mississauga, Ontario, Canada) consisting of a near infrared (NIR) laser light source and a NIR-sensitive digital camcorder. For measurements, the unit is positioned 30 to 40 cm from the area of interest. ICG, dissolved in water, is then injected as a bolus. The NIR light emitted by the laser light source induces ICG fluorescence. The fluorescence is recorded by a digital video camera, with optical filtering to block ambient and laser light so that, when desired, only ICG fluorescence is captured. Images can be observed on screen in real time (25 images/sec). The images can be reviewed and stored on the digital video camera or transferred to a computer or to storage media.

Example 2

The rat cavernous nerve model is well-recognized as a model for radical retropubic prostatectomy-associated neurogenic erectile dysfunction and has distinctive advantages over the other animal models. The rat cavernous nerves are single neural bundles that run alongside the prostate on either side. They are easily identified and are ideal neural bundles to evaluate the ability of neuro tracer to highlight pelvic nerves. Further, electrical stimulation is easily accomplished and yields reliable and reproducible results. Additionally, neurophysiological studies are feasible, and animal purchase, housing, and maintenance costs are low. The medical literature describes the successful use of Sprague-Dawley rats for the assessment of erectile dysfunction after cavernous nerve injury.

The animals are divided into three groups: Group I, placebo injection; group II intracavernous ICG injection; group III Fluorogold injection. Groups I-III are subdivided into 3 sub-groups, according to the timing for intraoperative evaluation of axonal fluorescent staining in cavernous nerves. Retrograde injection of placebo (distilled water) or fluorochromes, ICG or Fluorogold, is administered by intra-penile, sub-albugineal injection of 25 ul of ICG diluted in 100 µl of water for injection, per cavernous body.

Sprague-Dawley rats, 60 to 100 days old, weighing 275-325 grams are used. All animals are anesthetized using intraperitoneal injection of Ketamine/Xylazine (40-80 mg/kg and 5/10 mg/kg, respectively). No pre-anesthetic medications are used. When appropriate depth of anesthesia is reached, positioning of the animal takes place. All animals are fastened to a padded rack in the supine position using gauze knots to fix all four extremities to the rack equipped with heating device. Depth of anesthesia, regularity of respirations, and heart beat palpation are repeatedly checked. A pulse oximeter is used to monitor the animal.

Surgery/Procedure starts after appropriate preparation of surgical field by Povidone-Iodine scrub, 70% Isopropyl Alcohol and Povidone-Iodine solution. The surgical field includes the genital area, lower abdomen and perineum. The penis is squeezed out from prepuce, then stretched using finger grip at the glans and, when maximally stretched, a clamp used for atraumatic clamping in neurosurgical operation on brain aneurysms is placed at the root of the penis. This allows blood to pool inside cavernous bodies, an erection, and easier application of a 27 Gauge butterfly needle to sub-albugineal space bilaterally. Adequate placement is assured when blood is easily aspirated. 0.5 mg/kg of ICG and 1 mg/kg of Fluorogold diluted in distilled water to total volume of 50 µl is injected, 25 µl per cavernous body. A placebo group is injected using 25 µl of distilled water per cavernous body. Animals in all groups have an exploratory laparotomy through midline lower incision, with intraoperative identification of cavernous nerves. Midline incisions are made from umbilicus to pubis. Bowels and testicles, after their release from scrotal attachments, are packed back to upper abdomen. For better visualization of the pelvic structures, surgical loops with 3.8× magnification are used. In all animals, pelvic ganglion and cavernous nerves are identified bilaterally. The pressure at the level of penile base is held for 15 minutes to allow better penetration of injected fluorochromes into neural endings in cavernous bodies. After release of the clamps, the 27 Gauge needles are removed, but a slight pressure by fingers at the injection sites is maintained for 3-5 minutes to prevent extravasation. Buprenorphine (0.01-0.05 mg/kg) is administered intraoperatively and then as needed to control pain.

Post-procedurally, optimal recovery is routinely performed in all animals: animals are kept warm using warming packs, pads and lamps, the animals are placed on a paper towel, and are rotated from side to side every 15 minutes until they are able to maintain sternal recumbence. 3-4 ml of Lactated Ringer solution, warmed to 37° C., is administered subcutaneously, unilaterally in the flank region. This prevents postoperative dehydration of the animal. Animals are attended at all times during postoperative recovery. The animals are then returned to cages, and hydration is assessed on a daily basis with desired volume of 60-80 ml/kg/day, which translates to approximately 30 ml of fluids per 300 g animal, per day. Similarly, a 300 gram rat which is estimated to be 10% dehydrated would need to have 300 g ×0.10=30 ml of fluids replaced per day. Analgesia is used for all animals for postoperative pain. Animals are checked for signs of pain every 6 hours during first 24 hours post-surgery and then every 12 hours until sacrifice surgery. Signs of acute pain are guarding (protecting the painful area), vocalization, especially when the animal moves or the painful area is touched, licking, biting, scratching or shaking a particular area, restlessness, such as pacing and repeatedly lying down and getting up again (stereotypic-like behavior), lack of mobility as seen with joint, colic or gut pain or an unusual gait posture during movement, failure to groom, causing an unkempt appearance (rats accumulate red porphyrin around the eyes when they fail to groom properly), abnormal resting postures in which the animal appears to be sleeping or is hunched up and cannot get comfortable, failure to show normal patterns of inquisitiveness or alertness, loss of appetite or reduction in water consumption, and changes in behavior or signs of aggression.

To perform neurostimulation and harvesting of cavernous nerves and cavernous bodies, the rats undergo a second surgery (non-survival) and postmortem harvesting at chosen timepoints after fluorochrome injection.

Anesthesia identical to the first procedure is administered and then appropriate skin preparation for surgery is performed. The same level of incision is used in second surgery/harvesting procedure. The bladder and prostate are exposed as in the first surgery. The penis is denuded of skin and the prepuce circumcised. Cavernous nerves, located lateral to urethra and prostate bilaterally, are identified using the SPY® Imaging System (Novadaq Technologies, Inc. Toronto, Canada) and isolated for electrode placement. A stainless-steel bipolar electrode with parallel hooks (1 mm apart) is placed around a cavernous nerve and positioned by micromanipulator. The electrode cable is attached to a Grass S48 stimulator (Quincy, Mass.), with stimulation parameters 16 Hz, 5 msec duration, 0.5 to 4 volts. To monitor the intracavernous pressure (ICP), a heparinized (100 units per 1 ml NS) 24 gauge angiocath (Insyte-N, Becton Dickinson Vascular Access, Sandy, Utah), attached to polyethylene-50 tubing, is inserted in the rat's right cavernous body. A cannula inserted to the right cavernous body is connected to a pressure transducer and an amplifier unit (Harvard Apparatus, Holliston, Mass). The amplifier is connected to a data acquisition module (DI-190, Dataq Instruments, Akron, Ohio). The data is recorded on a computer with Windaq/Lite recording software (Dataq). Similarly, Central Arterial Pressure (CAP) is measured after appropriate placement of silicone tube into common carotid artery identified just lateral to the trachea. This allows measurement of the cavernous/central arterial pressure ratio and accurate assessment of erection in animal after cavernous nerve stimulation. When ICP measurements are completed, the animal is euthanized by performing elongation of abdominal incision with opening of the chest and use of large vascular clip to ligate aorta and vena cava at the exit/entrance from/to the heart. Death of the animal is confirmed using pulse oximeter and observation of complete absence of heart contractions. Both cavernous nerves are harvested in full length after appropriate exposure of the pelvic structures bilaterally, close to the pubis. Nerves are transected and an excised segment is fixed in 1.5 ml, 5% formalin, and contralateral segment is frozen in liquid nitrogen for further analysis.

Already denuded cavernous bodies are transected close to their roots and divided tangentially. Identical fixation and storage are used for cavernous bodies as for cavernous nerves. At the end of non-survival surgery cavernous nerves are harvested as well as cavernous bodies using NS and 10% Formaldehyde adequately marked tubes. Half of the specimen is placed into Formalin Aldehyde and half into NS. These are sent for pathological assessment of the structures for presence of fluorochrome in cavernous bodies and presence of axonal tracer/fluorochrome in cavernous nerves. Electronic microscopy is used to assess subcellular integrity of the neural and myovascular structures.

Example 3

To determine whether crural injections of dye would also result in the ability to image the cavernous nerves, 0.22 ml 1 f 0.25 mg/ml of ICG was injected subalbugineally into both crura of 22 rats. The area was examined for retrograde axonal transport at different time points, using a NIRF intraoperative imaging system (SPY®, Novadaq Technologies Inc., Mississauga, Ontario, Canada) that illuminates tissues with a 805 nm laser and captures images with a camera sensitive to infrared fluorescence. Near infrared microscopy and conventional histology were used to confirm the macroscopically identified fluorescent structures.

Intracrural injection of ICG permitted identification of the nerves at 6, 8, 12, 18, 24 and 36 hours post-operatively. (These were specific time points at which examinations were made. It can be assumed that the nerves would have also fluoresced and therefore permitted identification of the nerves at times, such as 20 hours and 30 hours, between those at which the nerves were examined.) Although other penile structures fluoresced for extended periods, fluorescence of the cavernous nerves was not detectable at longer post-injection periods (e.g., 30 days). The highest intensity was achieved at 18 and at 24 hours post-injection. NIRF and hematoxylin and eosin (H&E) staining were used to confirm that the fluorescence observed macroscopically coincided with the cavernous nerves.

Example 4

Figure 1D:
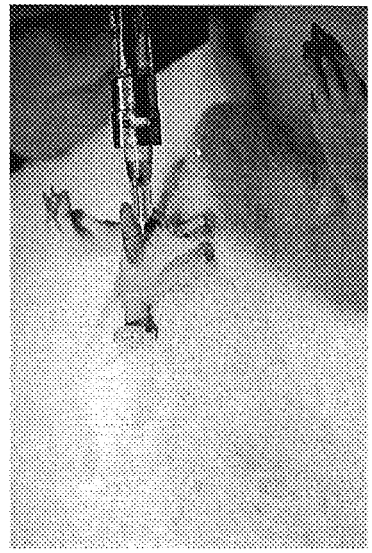

The cavernous nerves of rats were imaged using ICG following the protocol set forth in the preceding Examples. FIGS. 1a, b, and c show the exposing of the penis and injection of ICG into the crura of the cavernous bodies. FIG. 1d shows the penile crura and cavernous nerves under near infrared (NIRF) illumination following injection of ICG.

Figure 2:
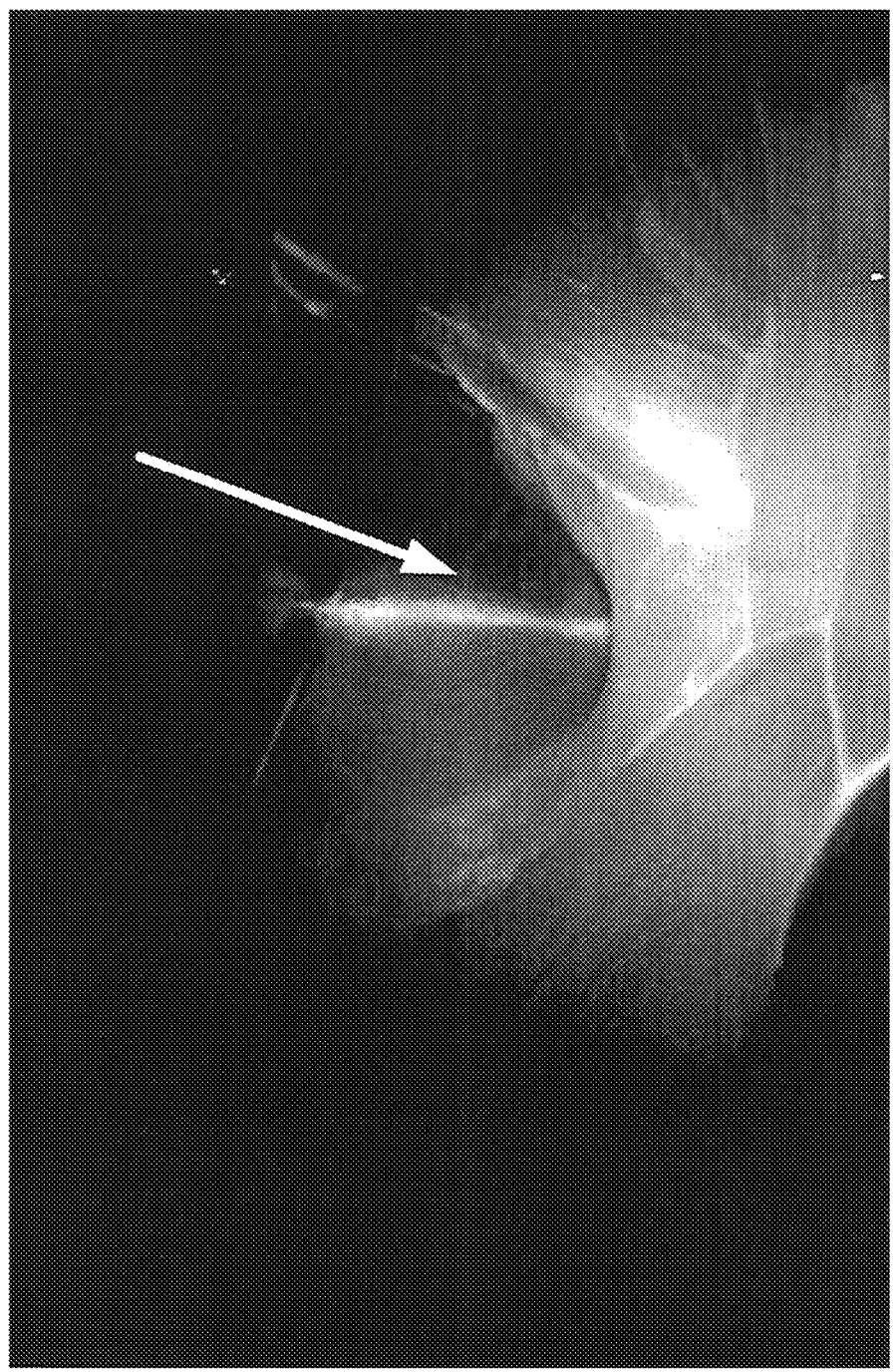
FIG. 2.
Figure 3:
FIG. 3.
Figure 4:
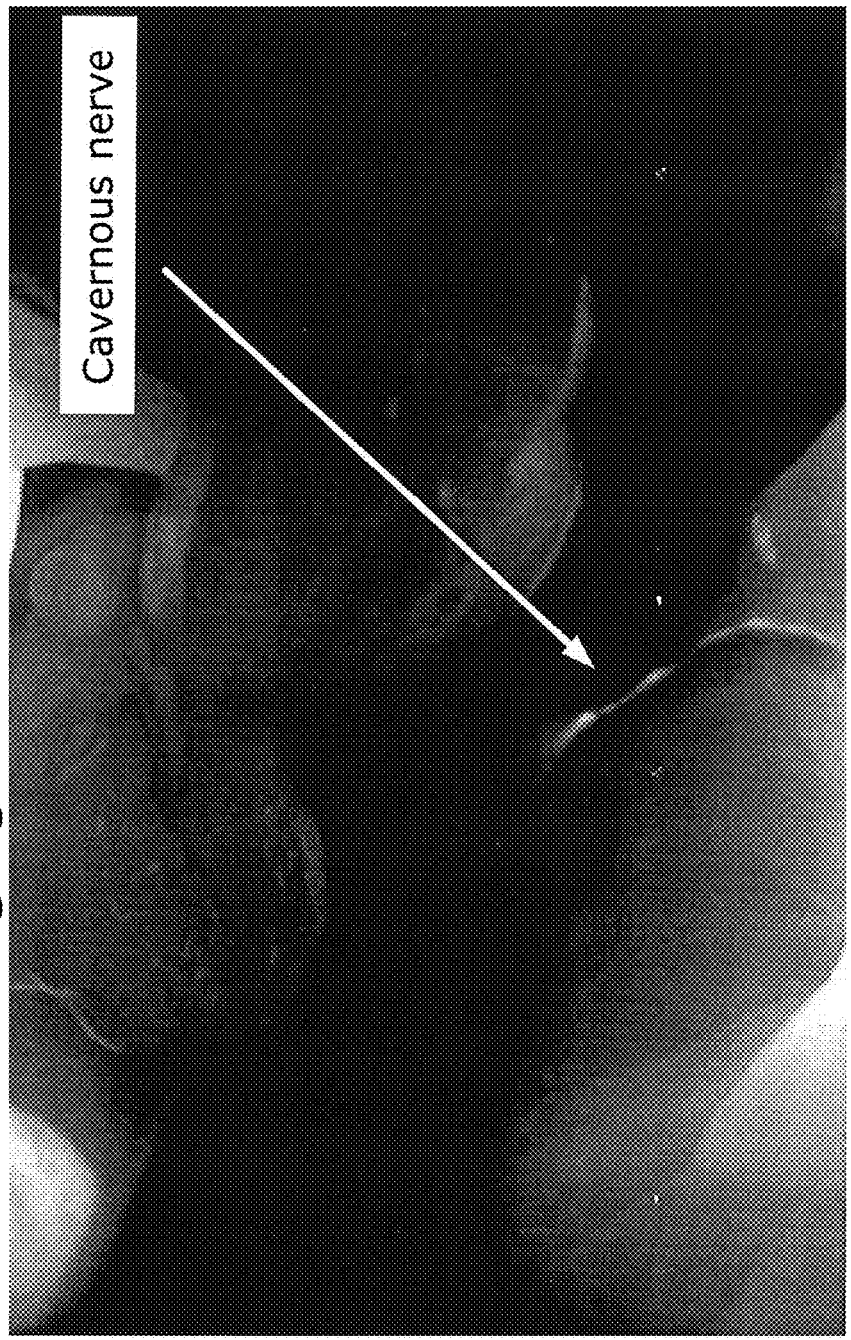
FIG. 4.

FIG. 2 shows a cavernous nerve under NIRF. The white arrow points to the nerve. In a series of studies, nerves were identified in situ at 6, 8, 12, 18, 24, and 36 hours post ICG injection. The highest fluorescent intensity was noted at 18 and at 24 hours post injection. The fluorescent nerves were then excised. NIRF and hematoxylin and eosin (H&E) staining were used to confirm that the fluorescence observed macroscopically coincided with the cavernous nerves. FIG. 3 shows a hook electrode hooked around a cavernous nerve under NIRF, after ICG injection as described above. FIG. 4 shows NIRF illumination of a cavernous nerve (arrow) from an animal injected with ICG as described above.

Figure 5A:
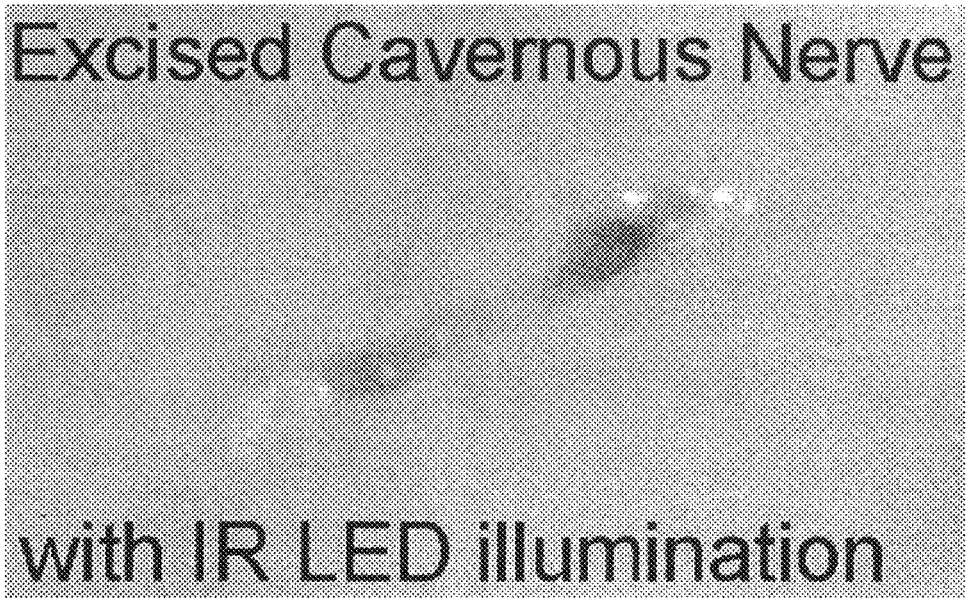
FIGS. 5a and 5b.
Figure 5B:
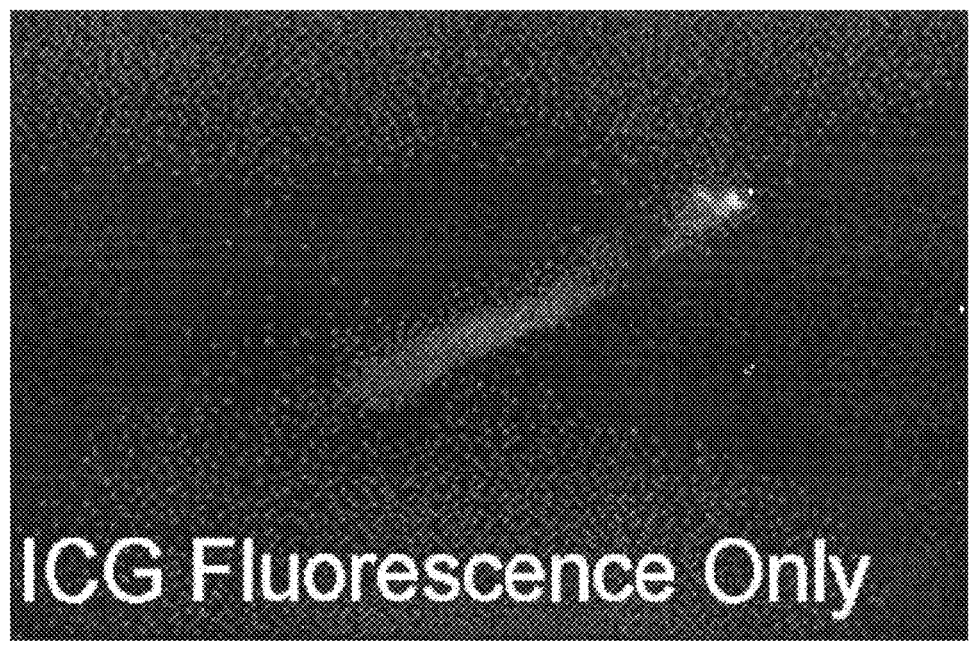

FIGS. 5a and 5b are photographs of a cavernous nerve excised from an animal injected with ICG as described above. FIG. 5a shows the nerve under infrared and LED illumination. FIG. 5b shows the same nerve under NIRF alone. The surgeon can alternate at will between visualizing the nerve under normal illumination (with or without infrared illumination) and by fluorescence induced by NIRF illumination.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of determining the location of a cavernous nerve in a subject during a surgical operation, comprising:
    a) between 1 hour and 30 hours prior to said surgical operation, injecting indocyanine green (ICG) into a cavernous body of a penis or a clitoris or an epidural space, wherein the ICG is taken up by or proceeds along the path of said cavernous nerve;
    b) exposing said cavernous nerve to illumination comprising an excitation wavelength of ICG, thereby causing said ICG in or along the nerve or portion thereof to fluoresce; and
    c) detecting the fluorescence of said ICG, thereby determining the location of said nerve during said surgical operation.

2. The method of claim 1, wherein said injection into said cavernous body is into a crus of said cavernous body.

3. The method of claim 1, wherein said determination of the location of said nerve is used to avoid transecting said nerve.

4. The method of claim 1, wherein said surgical operation is a radical prostatectomy.

5. The method of claim 1, wherein said surgical operation is a radical hysterectomy.

6. The method of claim 1, wherein said nerve or said portion of said nerve is visualized on a image display, thereby permitting determination of the location of said nerve or portion of said nerve.

7. The method of claim 1, wherein said exposing of said nerve to excitation wavelength is by a laparoscopic instrument.

8. The method of claim 1, wherein said dye is a dye which fluoresces when exposed to near infrared light.

9. The method of claim 1, wherein the subject is a human.

10. The method of claim 1, wherein said ICG is administered between about 18 hours and about 24 hours before said surgical operation.

11. The method of claim 1, wherein said ICG is administered between about 6 hours and about 24 hours before said surgical operation.

12. The method of claim 3, wherein the cavernous nerve is the small cavernous nerve.

13. The method of claim 3, wherein the cavernous nerve is the large cavernous nerve.

* * * * *